US012688907B2

(12) United States Patent
Yekhanin et al.

(10) Patent No.: US 12,688,907 B2
(45) Date of Patent: Jul. 21, 2026

(54) TRACE RECONSTRUCTION FROM READS WITH INDETERMINANT ERRORS

(71) Applicant: MICROSOFT TECHNOLOGY LICENSING, LLC, Redmond, WA (US)

(72) Inventors: Sergey Mikhailovich Yekhanin, Redmond, WA (US); Miklos Zoltan Racz, Princeton, NJ (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 259 days.

(21) Appl. No.: 18/166,386

(22) Filed: Feb. 8, 2023

(65) Prior Publication Data

US 2023/0238080 A1 Jul. 27, 2023

Related U.S. Application Data

(62) Division of application No. 16/105,349, filed on Aug. 20, 2018, now Pat. No. 11,600,360.

(51) Int. Cl.
| | |
|---|---|
| *G16B 30/00* | (2019.01) |
| *G06F 40/166* | (2020.01) |
| *G06F 40/279* | (2020.01) |
| *G16B 40/00* | (2019.01) |
| *G16B 40/20* | (2019.01) |

(52) U.S. Cl.
CPC ........... *G16B 30/00* (2019.02); *G06F 40/166* (2020.01); *G06F 40/279* (2020.01); *G16B 40/00* (2019.02); *G16B 40/20* (2019.02)

(58) Field of Classification Search
CPC ........ G16B 30/00; G16B 40/00; G16B 40/20; G16B 20/20; G16B 40/30; G16B 30/10; G06F 40/166; G06F 40/279
See application file for complete search history.

(56) References Cited

FOREIGN PATENT DOCUMENTS

| | | |
|---|---|---|
| CN | 106021986 A | 10/2016 |
| CN | 108138227 A | 6/2018 |
| WO | WO-2017189469 A1 * 11/2017 .......... G06F 11/3466 |

OTHER PUBLICATIONS

Deamer, D., Akeson, M. and Branton, D. Three decades of nanopore sequencing. Nature Biotechnology, 34(5), pp. 518-524. (Year: 2016).*
Chin, C.S., Alexander, D.H., Marks, P., Klammer, A.A., Drake, J., Heiner, C., Clum, A., Copeland, A., Huddleston, J., Eichler, E.E. and Turner, S.W. Nonhybrid, finished microbial genome assemblies from long-read SMRT sequencing data. Nature methods, 10(6), pp. 563-569. (Year: 2013).*
Yazdi, S.H.T., Gabrys, R. and Milenkovic, O. Portable and error-free DNA-based data storage. Scientific reports, 7(1), p. 5011. (Year: 2017).*
Intimation of the grant Received in Indian Patent Application No. 202117004783, mailed on Aug. 9, 2024, 01 page.
U.S. Appl. No. 16/105,349, filed Aug. 20, 2018.
Second Office Action Received for Chinese Application No. 201980054964.5, mailed on Jan. 15, 2025, 6 pages (English Translation Provided).
First Office Action Received for Chinese Application No. 201980054964.5, mailed on Jun. 27, 2024, 13 pages (English Translation Provided).
Vaser, et al., "Fast and accurate de novo genome assembly from long uncorrected reads," Genome research, 2017, pp. 737-746.
Communication 94(3) Received for European Application No. 19739808.4, mailed on Mar. 18, 2024, 8 pages.

* cited by examiner

*Primary Examiner* — Olivia M. Wise
*Assistant Examiner* — Janna Nicole Schultzhaus
(74) *Attorney, Agent, or Firm* — Benjamin Keim; Newport IP, LLC

(57) ABSTRACT

Polynucleotide sequencing generates multiple reads of a polynucleotide molecule. Many or all of the reads contain errors. Trace reconstruction takes multiple reads generated by a polynucleotide sequencer and uses those multiple reads to reconstruct accurately the nucleotide sequence of the polynucleotide molecule. Some reads may contain errors that cannot be corrected. Thus, there may be reads that can be used throughout their entire length and other reads that have indeterminant errors which cannot be corrected. Rather than discarding the entire read when an indeterminant error is found, the portion of the read with the error is skipped and the sequence of the read following the error is used to reconstruct the trace. The amount of the read skipped is determined by the location of subsequence after the error that matches a consensus sequence of the other reads. Analysis resumes at a location determined by the location of the match.

18 Claims, 16 Drawing Sheets

Specification includes a Sequence Listing.

100

SUBSTITUTION

DELETION

INSERTION

INDETERMINANT ERROR

INDETERMINANT
ERROR 604

CENTERED

800

ALIGNMENT ANCHOR 806

EQUALLY SPACED

802

808          810          812

CENTER-BIASED SPACING

804

820          814    816    818          822

ALIGNMENT ANCHOR 902

900

←————906————

←————910————

————904————→

————908————→

PARTIAL CONSENSUS SEQUENCE 912

PARTIAL CONSENSUS SEQUENCE 914

JOINED CONSENSUS SEQUENCE 916

CONSENSUS OUTPUT SEQUENCE
W/O ANCHOR 918

1000

Figure 12B:
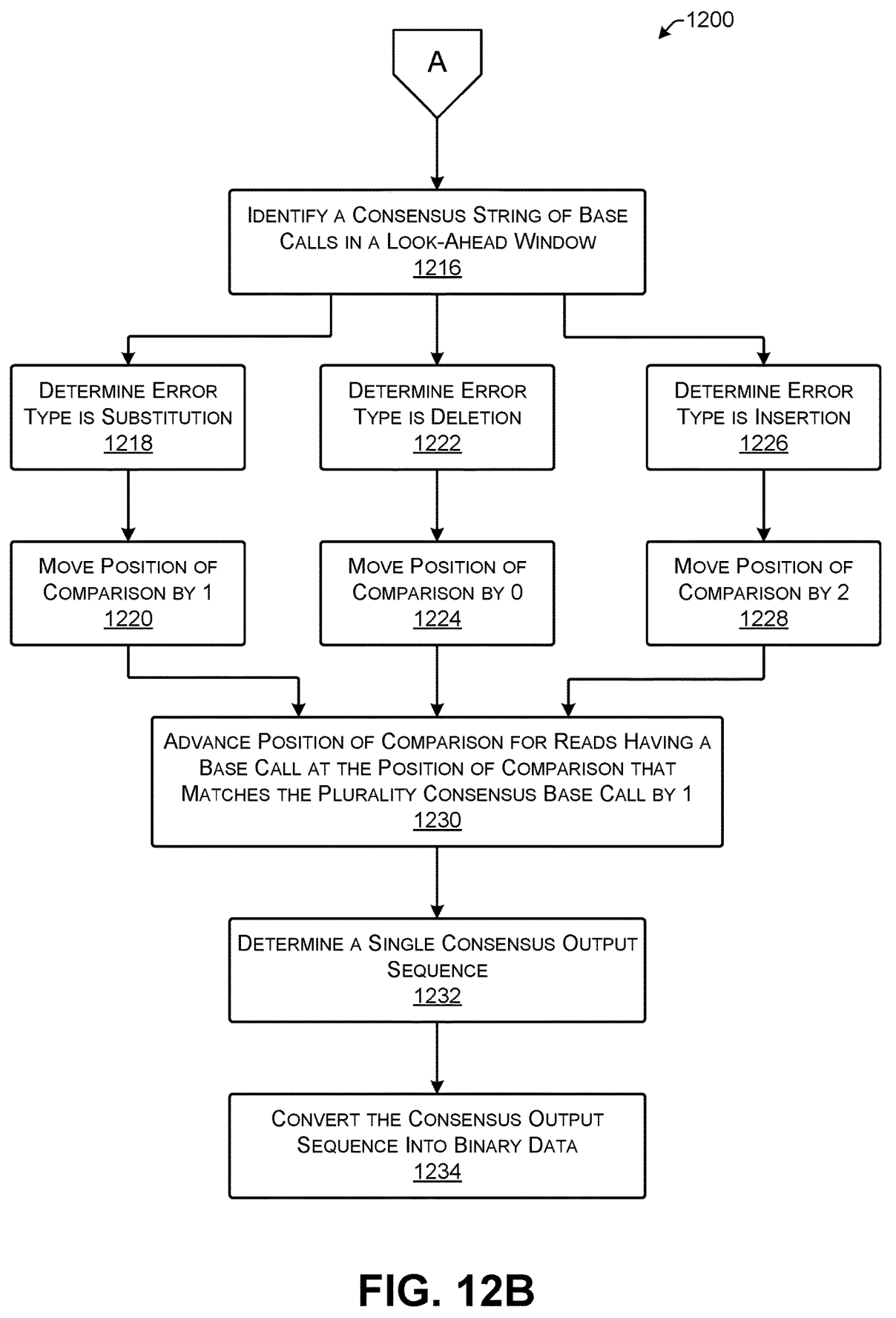

1200

A

IDENTIFY A CONSENSUS STRING OF BASE
CALLS IN A LOOK-AHEAD WINDOW
1216

DETERMINE ERROR
TYPE IS SUBSTITUTION
1218

DETERMINE ERROR
TYPE IS DELETION
1222

DETERMINE ERROR
TYPE IS INSERTION
1226

MOVE POSITION OF
COMPARISON BY 1
1220

MOVE POSITION OF
COMPARISON BY 0
1224

MOVE POSITION OF
COMPARISON BY 2
1228

ADVANCE POSITION OF COMPARISON FOR READS HAVING A
BASE CALL AT THE POSITION OF COMPARISON THAT
MATCHES THE PLURALITY CONSENSUS BASE CALL BY 1
1230

DETERMINE A SINGLE CONSENSUS OUTPUT
SEQUENCE
1232

CONVERT THE CONSENSUS OUTPUT
SEQUENCE INTO BINARY DATA
1234

IDENTIFY THE START OF A PORTION OF A
READ THAT CONTAINS A BURSTY ERROR
1302

IDENTIFY THE END OF THE PORTION OF
THE READ THAT CONTAINS THE BURSTY
ERROR 1304

OMIT THE PORTION OF THE READ THAT
CONTAINS THE BURSTY ERROR
1306

GENERATE A CONSENSUS OUTPUT
SEQUENCE WITH PORTIONS OF THE READ
FROM EITHER SIDE OF THE BURSTY ERROR
1308

TRACE RECONSTRUCTION FROM READS WITH INDETERMINANT ERRORS

CROSS-REFERENCE TO RELATED APPLICATION

This application is divisional of U.S. patent application Ser. No. 16/105,349, filed Aug. 20, 2018, the content of which application is hereby expressly incorporated herein by reference in its entirety.

BACKGROUND

Much of the world's data today is stored on magnetic and optical media. Tape technology has recently seen significant density improvements with single tape cartridges storing 185 TB and is the densest form of storage available commercially today, at about 10 GB/mm³. Recent research reported the feasibility of optical discs capable of storing 1PB, yielding a density of about 100 GB/mm³. Despite this improvement, storing a zettabyte ($2^{70}$ bytes or a billion terabytes) of data would still take many millions of units, and use significant physical space. But storage density is only one aspect of storage media; durability is also important. Rotating disks are rated for 3-5 years, and tape is rated for 10-30 years. Long-term archival storage requires data refreshes, both to replace faulty units and to refresh technology.

Demand for data storage is growing exponentially, but the capacity of existing storage media is not keeping up. Polymers of deoxyribose nucleic acid (DNA) are capable of storing information at high density. The theoretical density limit is 1 exabyte/mm³ ($10^9$ GB/mm³). Less than 100 grams of DNA could store all the human-made data in the world today. DNA is also long lasting, with an observed half-life of over 500 years under certain storage conditions. Thus, DNA is appealing as an information storage technology because of its high information density and longevity. A further advantage of DNA as a storage media is its continued relevance. Operating systems and standards for storage media will change, potentially making data on older storage systems inaccessible. But DNA-based storage has the benefit of eternal relevance: as long as there is DNA-based life, there will be strong reasons to maintain technology that is able to read and manipulate DNA.

Although it has advantages, a DNA storage system must overcome several challenges. For example, DNA synthesis, degradation during storage, and sequencing are all potential sources of errors. Thus, a DNA sequence output by a sequencer may be different from the DNA sequence originally provided to an oligonucleotide synthesizer.

SUMMARY

This Summary is provided to introduce a selection of concepts in a simplified form that are further described below in the Detailed Description. This Summary is not intended to identify key features or essential features of the claimed subject matter nor is it intended to be used to limit the scope of the claimed subject matter.

Binary data of the kind currently used by computers to store text files, audio files, video files, software, and the like can be represented as a series of nucleic acids in a polynucleotide (i.e., DNA or ribonucleic acid (RNA)). There are multiple techniques for representing the 0 and 1 of binary data as a series of nucleotides. Multiple techniques are known to persons of ordinary skill in the art. A polynucleotide sequence is designed to hold the binary data and then synthesized with an oligonucleotide synthesizer. The synthesized polynucleotide is placed into storage, and it is ultimately read by a polynucleotide sequencer. The data generated by the polynucleotide sequencer is decoded to recover the stored binary data. The machines that write and read the sequences of polynucleotides are not 100% accurate and introduce errors. Some types of errors, such as insertions, deletions, or substitutions of a nucleotide, can be identified and corrected. Other types of errors, in particular "bursty" errors in which there are multiple errors in a localized "burst" adjacent or close to each other, can be difficult or impossible to correct. Thus, with some decoding techniques sequence reads that include bursty errors may be unusable. This disclosure provides techniques for extracting useful information from reads of polynucleotide sequences that include bursty errors or other types of indeterminant errors.

Polynucleotide sequencing of a batch of polynucleotides may generate a total length of reads that is many times longer than the total length of all the polynucleotides in the sequencing batch. This is referred to as "depth of coverage." A depth of coverage greater than one (e.g., 10×, 20×, 30×, etc.) indicates that, on average, each polynucleotide is provided to the sequencer the number of times indicated by the depth of coverage. Because this is an average value, some polynucleotides may not be sequenced at all while others are sequenced many times more than the coverage level. For a single sequencing run, the depth of coverage may be calculated by the total number of base pairs sequenced divided by the total length of polynucleotides provided to the machine for sequencing. Each of the multiple sequencing reads of the same polynucleotide may have a slightly different sequence. Reads that are similar to each other, and thus, were likely all generated by sequencing the same polynucleotide, can be grouped together in a cluster for further analysis. The number of reads in a cluster is, on average, the same as the depth of coverage.

Analysis of the reads in the cluster is performed to identify a single consensus output sequence from the multiple reads in the cluster. This type of analysis may be referred to as "trace reconstruction." The consensus output sequence is more likely to represent the actual sequence of nucleotides in the source polynucleotide molecule than any of the individual reads. Techniques for creating a consensus sequence from multiple reads are known to those of skill in the art. Some techniques identify errors in single positions of a read and correct for the errors based on the sequences of the other reads at the same position. Errors that may be identified and corrected include insertions, deletions, and substitutions. However, when multiple errors are close together, such as an insertion followed by a substitution and then two deletions, current techniques for creating consensus output sequences are unable to correctly identify the errors and the entire read may be ignored when determining the consensus output sequence. Rather than ignoring or discarding data from reads that have indeterminant errors, the techniques discussed in this disclosure include identifying a position of an indeterminant error, skipping over the portion of the read that contains the indeterminant error, and using subsequent base calls in the read to determine the consensus output sequence.

An indeterminant error may be identified at a position in a read that does not match the consensus sequence derived from the other reads in the same cluster and for which the type of error cannot be determined. For example, if a given base call in a read is different from the base calls of all the other reads at that same position but that difference is unable to be identified as an insertion, deletion, or substitution error, then that base call may be characterized as an indeterminant error. A set number of positions may be skipped over and a search window farther down the read is evaluated to determine if there is a matching subsequence between the read with indeterminant error and the other reads in the cluster. Each subsequence of a given length within the search window may be evaluated to determine if it matches with the sequences from the other reads. The matching may be determined in part by matching between the base calls in the read with indeterminant error and the base calls of the consensus sequence. The matching may additionally be determined by comparing the base calls of the read with an indeterminant error with a simple plurality vote of the other reads. A simple plurality vote considers the most common base call at a given position without accounting for errors such as insertions, deletions, and substitutions.

If a match is found, then a single position within the matching subsequence is taken as the candidate position and the subsequent position adjacent to the candidate position is used as a position of comparison to resume using the read for determining the consensus output sequence. Thus, positions in the read before the indeterminant error may be used together with some or all of the other reads in the cluster to determine a part of the consensus output sequence. The part of the read with the indeterminant error and some number of positions following the indeterminant error are ignored thus, the consensus output sequence for these positions is determined from other reads in the cluster. After the candidate position is located, the next position is again used together with other reads in the cluster to determine the consensus output sequence. Therefore, rather than ignoring all the data provided by the read that includes an indeterminant error, only a portion of that read in the vicinity of the indeterminant error is ignored and parts of the read both before and after the error may be used for determination of the consensus output sequence.

Alignment of the multiple reads in a cluster may be based on the first position in the reads or the last position in the reads. As generation of a consensus output sequence proceeds position-by-position (e.g., "front" to 'back" or "back" to "front"), errors and uncertainty may accumulate due to insertions and deletions that shift the reads out of phase with respect to each other. Known sequences intentionally inserted into all of the reads at the time of synthesis function as alignment anchors and provide a reference location other than the ends to realign the multiple reads. Thus, the multiple reads in a cluster may be aligned relative to each other based on alignment anchors as well as based on the first position and the last position of the reads. The reads may be designed to include one or more alignment anchors. Because the alignment anchors include alternative alignment points besides the beginning and ends of the reads, the reads may be split into shorter segments at the alignment anchors and each of the shorter segments may be separately evaluated to determine a consensus output sequence. The consensus output sequences for each of the shorter segments may be rejoined to create a single consensus output sequence for the full length of the original reads.

Specific implementations and examples in this disclosure may refer only to DNA; however, it is to be understood that the contents of this disclosure apply equally to any polynucleotide including DNA, RNA, DNA-RNA hybrids, as well as polynucleotides that include synthetic or unnatural bases.

DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items.

FIGS. 12A and 12B show an illustrative process for generating binary data from reads received from a polynucleotide sequencer.

DETAILED DESCRIPTION

Figure 1:
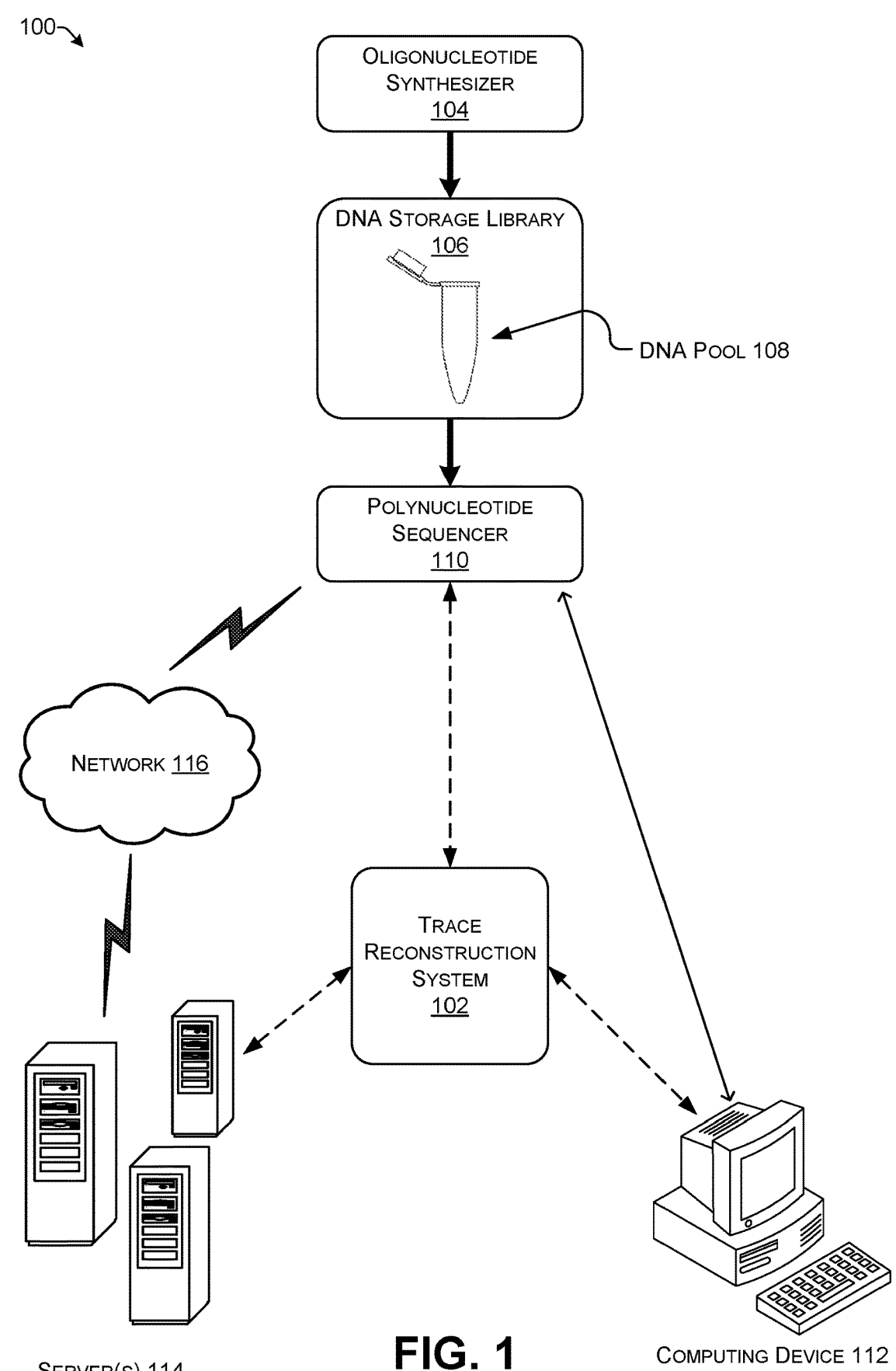
FIG. 1 shows an illustrative architecture for operation of a trace reconstruction system.

As mentioned above, DNA has great potential as a storage media for digital information. However, dealing with errors that may corrupt the data is one of the challenges of using DNA to store digital data. There are many steps involved in converting digital data into synthetic DNA molecules and then recovering the digital data from the synthetic DNA molecules. The techniques described in this disclosure provide techniques for using some of the information in a DNA read when that read includes an indeterminant error.

The term "DNA strands," or simply "strands," refers to DNA molecules. As used herein, "DNA reads," "sequence reads," or simply "reads" refer to strings of data generated by a polynucleotide sequencer when a polynucleotide sequencer reads the sequence of a DNA strand. Because the reads are strings of data they may also be referred to as "strings." However, reads produced by polynucleotide sequencers frequently contain errors, and thus, do not represent the structure of DNA strands with 100% accuracy.

Fortunately, most DNA sequencing technologies are capable of producing multiple reads of a DNA strand. The reads are referred to as "noisy reads" because each likely contains one or more errors that have a distribution that is approximately random. A given read may also be error free but it is not possible to know which reads are error free and which contain errors except with reference to each other. The techniques of this disclosure use the multiplicity of different noisy reads for a single DNA strand to create a consensus output sequence that is likely to represent the true sequence of the DNA strand. The consensus output sequence is a string of data similar to any of the reads, but the consensus output sequence is generated from analysis of the reads rather than being output directly from a polynucleotide sequencer. The process of going from many noisy reads to one, presumably accurate, consensus output sequence is referred to as "trace reconstruction."

Naturally occurring DNA strands consist of four types of nucleotides: adenine (A), cytosine (C), guanine (G), and thymine (T). A DNA strand, or polynucleotide, is a linear sequence of these nucleotides. The two ends of a DNA strand, referred to as the 5' and 3' ends, are chemically different. DNA sequences are conventionally represented starting with the 5' nucleotide end. The interactions between different strands are predictable based on sequence: two single strands can bind to each other and form a double helix if they are complementary: A in one strand aligns with T in the other, and likewise for C and G. The two strands in a double helix have opposite directionality (5' end attached to the other strand's 3' end), and thus, the two sequences are the "reverse complement" of each other. Two strands do not need to be fully complementary to bind to one another. Ribonucleic acid (RNA) has a similar structure to DNA and naturally occurring RNA consists of the four nucleotides A, C, G, and uracil (U) instead of T. Discussions in this disclosure mention only DNA for the sake of brevity and readability, but RNA may be used in place of or in combination with DNA.

The trace reconstruction problem may be set out using mathematical notation as follows. Let $\Sigma$ denote a finite alphabet, for instance, $\Sigma=\{A, C, G, T\}$. Let $X \in \Sigma^n$ be a sequence of interest, which can be arbitrary or random. The goal is to reconstruct the sequence of the DNA strand X exactly from a collection of noisy reads.

Some sequencing technologies such as sequencing-by-synthesis (discussed more below) have an error profile in which the noise is distributed independently at least to a degree. Thus, the noise can be modeled as independent and identically distributed (i.i.d.) throughout the strands. This type of noise can be created with synthetic test data. To do so, let $Y_1, Y_2, \ldots, Y_m$ be i.i.d. sequences obtained from X in the following way. Let $p_d$, $p_i$ and $p_s$ denote deletion, insertion, and substitution probabilities, respectively, such that $p=p_d+p_i+p_s \in [0, 1]$. To obtain a noisy read Y, start with an empty string, and for a position of comparison $j=1, 2, \ldots, n$, do the following:

(no error) with probability 1-p, copy X[j] to the end of Y and increase j by 1;

(deletion) with probability $p_d$, increase j by 1;

(insertion) with probability $p_i$, copy X[j] to the end of Y, add a random symbol at the end of Y, and increase j by 1;

(substitution) with probability $p_s$, add a random symbol at the end of Y and increase j by 1.

Other sequencing technologies such as nanopore sequencing (discussed more below) have a different error profile in which the errors are not independently distributed but tend to be clustered so that if one error is present it is more likely that other errors are nearby. Nanopore sequencing has more errors than sequencing-by-synthesis. About 12% as compared to about 1-2%. This can create "bursts" of errors in the string by creating a localized high-error region. In addition to single position errors, nanopore sequencing results may have larger errors such as transposition of neighboring blocks of bases.

Identifying a single consensus sequence from a plurality of noisy reads—trace reconstruction—outputs an estimate read X̂ which is the estimate for the true sequence X of the DNA strand. The estimate is created from a number m of noisy reads Y. Thus, $\hat{X}=\hat{X}(Y_1, Y_2, \ldots, Y_m)$. The goal is to exactly reconstruct X, i.e., to minimize $\mathbb{P}(\hat{X} \neq X)$. Minimizing the probability that X̂ is different from X may be done by using as many parts of the noisy reads Y while accounting for or ignoring errors in the noisy reads.

FIG. 1 shows an illustrative architecture 100 for implementing a trace reconstruction system 102. Briefly, digital information that is intended for storage as DNA molecules is converted into information representing a string of nucleotides. The information representing the string of nucleotides (i.e., a string of letters representing an order of nucleotide bases) is used as DNA-synthesis templates that instruct an oligonucleotide synthesizer 104 to chemically synthesize a DNA molecule nucleotide by nucleotide. Artificial synthesis of DNA allows for creation of synthetic DNA molecules with arbitrary series of the bases in which individual monomers of the bases are assembled together into a polymer of nucleotides. The oligonucleotide synthesizer 104 may be any oligonucleotide synthesizer using any recognized technique for DNA synthesis. The term "oligonucleotide" as used herein is defined as a molecule including two or more nucleotides.

The coupling efficiency of a synthesis process is the probability that a nucleotide binds to an existing partial strand at each step of the process. Although the coupling efficiency for each step can be higher than 99%, this small error still results in an exponential decrease of product yield with increasing length and limits the size of oligonucleotides that can be efficiently synthesized at present to about 200 nucleotides. Therefore, the length of the DNA strands put into storage is around 100 to 200 base pairs (bp). This length will increase with advances in oligonucleotide synthesis technology.

The synthetic DNA produced by the oligonucleotide synthesizer 104 may be transferred to a DNA storage library 106. There are many possible ways to structure a DNA storage library 106. In addition to structure on the molecular level by appending identifying sequences to the DNA strands, a DNA storage library 106 may be structured by physically separating DNA strands into one or more DNA pools 108. Here the DNA pool 108 is shown as a flip top tube representing a physical container for multiple DNA strands. DNA strands are generally most accessible for manipulation by bio-technological techniques when the DNA is stored in a liquid solution. Thus, the DNA pool 108 can be implemented as a chamber filled with liquid, in many implementations water, and thousands, millions, or more individual DNA molecules may be present in a DNA pool 108.

Besides being in a liquid suspension, the DNA strands in the DNA storage library 106 may be present in a glassy (or vitreous) state, as a lyophilized product, as part of a salt, adsorbed on the surface of a nanoparticle, or another format. The structure of the DNA pools 108 may be implemented as any type of mechanical, biological, or chemical arrangement that holds a volume of liquid including DNA to a physical location. Storage may also be in a non-liquid form such as a solid bead or by encapsulation. For example, a single flat surface having a droplet present thereon, with the droplet held in part by surface tension of the liquid, even though not fully enclosed within a container, is one implementation of a DNA pool 108. The DNA pool 108 may include single-stranded DNA (ssDNA), double-stranded DNA (dsDNA), single-stranded RNA (ssRNA), double-stranded RNA (dsRNA), DNA-RNA hybrid strands, or any combination including use of unnatural bases.

DNA strands removed from the DNA storage library 106 may be sequenced with a polynucleotide sequencer 110. In some implementations, DNA strands may be prepared for sequencing by amplification using polymerase chain reaction (PCR) to create a large number of DNA strands that are identical copies of each other. The need for PCR amplification prior to sequencing may depend on the specific sequencing technology used. PCR may itself be a source of error, although at a much lower level than current sequencing technology. At present, PCR techniques typically introduce approximately one error per 10,000 bases. Thus, on average, for every 100 reads of 100 bases there will be one error that is the result of PCR. The errors introduced by PCR are generally distributed randomly so the trace reconstruction system is able to correct some PCR-induced errors.

As mentioned above, the polynucleotide sequencer 110 reads the order of nucleotide bases in a DNA strand and generates one or more reads from that strand. Polynucleotide sequencers 110 use a variety of techniques to interpret molecular information and may introduce errors into the data in both systematic and random ways. Errors can usually be categorized as substitution errors, where the real nucleotide is substituted with an incorrect base call (for example A swapping with G), insertions, or deletions, where a random base call is inserted (for example AGT becoming AGCT) or deleted (for example AGTA becoming ATA). Transpositions, which are swapping of longer regions of DNA, are another type of error. Each position in a read is an individual base call determined by the polynucleotide sequencer 110 based on properties sensed by components of the polynucleotide sequencer 110. The various properties sensed by the polynucleotide sequencer 110 vary depending on the specific sequencing technology used. A base call represents a determination of which of the four nucleotide bases—A, G, C, and T (or U)—in a strand of DNA (or RNA) is present at a given position in the strand. Sometimes the base calls are wrong, and this is a source of error introduced by sequencing. Polynucleotide sequencing includes any method or technology that is used to generate base calls from a strand of DNA or RNA.

A sequencing technology that can be used is sequencing-by-synthesis (Illumina® sequencing). Sequencing by synthesis is based on amplification of DNA on a solid surface using fold-back PCR and anchored primers. The DNA is fragmented, and adapters are added to the 5' and 3' ends of the fragments. DNA fragments that are attached to the surface of flow cell channels are extended and bridge amplified. The fragments become double stranded, and the double-stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase, and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection, and identification steps are repeated.

Another example of a sequencing technique that can be used is Nanopore sequencing. A nanopore is a small hole of the order of 1 nanometer in diameter. Immersion of a nanopore in a conducting fluid and application of a potential across the nanopore results in a slight electrical current due to conduction of ions through the nanopore. The amount of current that flows through the nanopore is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence.

Other sequencing technologies that are currently known include single molecule, real-time (SMRT™) technology from Pacific Biosciences, Helicos True Single Molecule Sequencing (tSMS), SOLiD™ technology available from Applied Biosystems, use of a chemical-sensitive field effect transistor (chemFET) array, and use of an electron microscope to read a sequence of nucleotide bases.

All technologies for sequencing DNA are associated with some level of error and the type and frequency of errors differ by sequencing technology. For example, sequencing-by-synthesis creates an error in about 2% of the base calls and the errors tend to be independently and identically distributed (i.i.d.). A majority of these errors are substitution errors. Nanopore sequencing has a much higher error rate of about 15 to 40% and most of the errors caused by this sequencing technology are deletions. Errors in sequences generated by Nanopore sequencing tend to be present in clusters so if a position has an error it is more likely that adjacent positions will too. Thus, the errors may be thought of as coming in "bursts." The error profile of a specific sequencing technology may describe the overall frequency of errors, distribution characteristics of errors, as well as the relative frequency of various types of errors.

In some implementations, the polynucleotide sequencer 110 provides quality information that indicates a level of confidence in the accuracy of a given base call. The quality information may indicate that there is a high level or a low level of confidence in a particular base call. For example, the quality information may be represented as a percentage, such as 80% confidence, in the accuracy of a base call. Additionally, quality information may be represented as a level of confidence that each of the four bases is the correct base call for a given position in a DNA strand. For example, quality information may indicate that there is 80% confidence the base call is a T, 18% confidence the base call is an A, 1% confidence the base call is a G, and 1% confidence the base call is a C. Thus, the result of this base call would be T because there is higher confidence in that nucleotide being the correct base call than in any of the other nucleotides. Quality information does not identify the source of an error but merely suggests which base calls are more or less likely to be accurate.

The polynucleotide sequencer 110 provides output, multiple noisy reads (frequently of multiple DNA strands), in electronic format to the trace reconstruction system 102. The output may include the quality information as metadata for otherwise associated with the reads produced by the polynucleotide sequencer 110.

The trace reconstruction system 102 may be implemented as an integral part of the polynucleotide sequencer 110. The polynucleotide sequencer 110 may include an onboard computer that implements the trace reconstruction system 102. Alternatively, the trace reconstruction system 102 may be implemented as part of a separate computing device 112 that is directly connected to the polynucleotide sequencer 110 through a wired or wireless connection which does not cross a network. For example, the computing device 112 may be a desktop or notebook computer used to receive data from and/or to control the polynucleotide sequencer 110. A wired connection may include one or more wires or cables physically connecting the computing device 112 to the polynucleotide sequencer 110. The wired connection may be created by a headphone cable, a telephone cable, a SCSI cable, a USB cable, an Ethernet cable, FireWire, or the like. The wireless connection may be created by radio waves (e.g., any version of Bluetooth, ANT, Wi-Fi IEEE 802.11, etc.), infrared light, or the like. The trace reconstruction system 102 may also be implemented as part of a cloud-based or network system using one or more servers 114 that communicate with the polynucleotide sequencer 110 via a network 116. The network 116 may be implemented as any type of communications network such as a local area network, a wide area network, a mesh network, an ad hoc network, a peer-to-peer network, the Internet, a cable network, a telephone network, and the like. Additionally, the trace reconstruction system 102 may be implemented in part by any combination of the polynucleotide sequencer 110, the computing device 112, and the servers 114.

Figure 2:
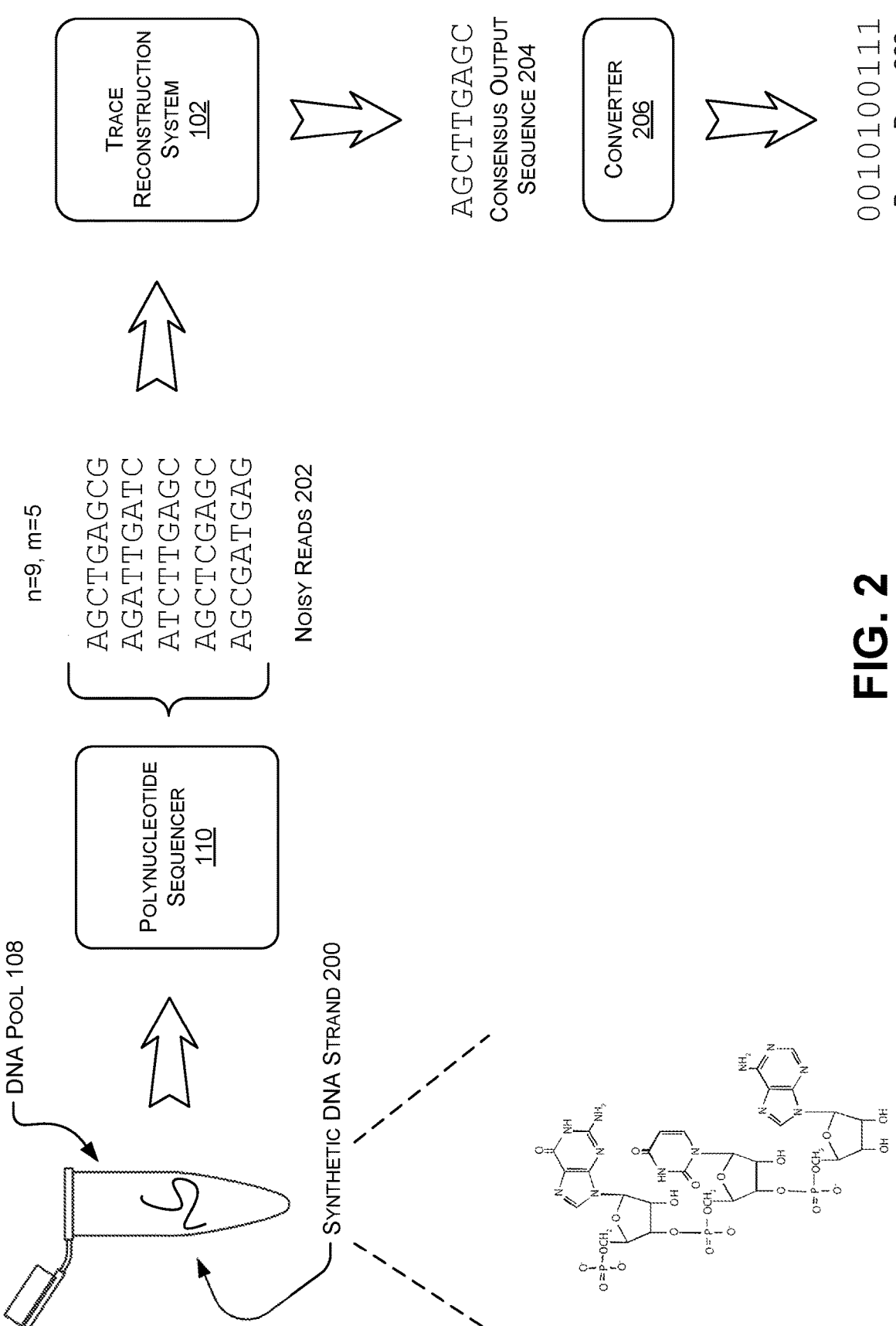
FIG. 2 is an illustrative schematic showing the use of a trace reconstruction system.

FIG. 2 shows the use of the trace reconstruction system 102 as part of the process of decoding information stored in a synthetic DNA strand 200. The synthetic DNA strand 200 is a molecule having a specific sequence of nucleotide bases. The synthetic DNA strand 200 may be stored in a DNA pool 108 as shown in FIG. 1. The synthetic DNA strand 200 may be present in the DNA pool 108 as a single-stranded molecule or may hybridize to a complementary ssDNA molecule to form dsDNA. The polynucleotide sequencer 110 produces an output of multiple noisy reads 202 from the single synthetic DNA strand 200. The number of reads is related to coverage depth of the sequencing. Greater depth of sequencing leads to on average more sequences generated from the DNA strand. Because of the errors in sequencing, it is likely that many of the multiple reads of the same DNA strand have different sequences. Each of the reads has a length (n) which in this example is nine corresponding to nine bases in the synthetic DNA strand 200. In actual sequencer data the noisy reads may have arbitrary lengths that are not all equal to each other. Deletions and insertions are one cause of variation in read length. For a given read, that read's length may be denoted as n, but n is not necessarily the same for all reads. In actual implementations, the length of the reads is likely to be between 100 and 200 due to current limitations on the maximum length of DNA strands that can be artificially synthesized. Locations on a read may be referred to as "positions" such as in this example going from position one to position nine. As used herein, "base" refers to a location of a given monomer in a DNA molecule while "position" refers to a location along a string of data such as a read. Thus, assuming no errors, the third base in the synthetic DNA strand 200 corresponds to the third position in a read generated by the polynucleotide sequencer 110.

The number (m) of noisy reads 202 provided to the trace reconstruction system 102 is five in this example. However, any number may be used. In some implementations, the number of noisy reads 202 provided to the trace reconstruction system 102 may be 10, 20, or 100. The number of noisy reads 202 provided to the trace reconstruction system 102 may be less than the total number of reads produced by the polynucleotide sequencer 110. A subset of the total number reads produced by the polynucleotide sequencer 110 may be selected at random or using heuristics for analysis by the trace reconstruction system 102. In addition to random selection, other techniques may be used for choosing which subset of reads are passed to the trace reconstruction system 102. For example, quality information may be used to identify m reads having the highest confidence in the base calls from all of the reads generated by the polynucleotide sequencer 110. In some implementations, only reads with certain lengths are selected.

The trace reconstruction system 102 analyzes the noisy reads 202 according to the techniques of this disclosure and generates a consensus output sequence 204. The consensus output sequence 204 represents the sequence of nucleotides in the synthetic DNA strand 200 with less error than any of the individual noisy reads 202 and ideally with no error.

A converter 206 converts the consensus output sequence 204 into binary data 208, thereby retrieving the digital information stored in the DNA storage library 106. The converter 206 may use additional error correction techniques to correct any errors that may remain in the consensus output sequence 204. Thus, it is not necessary for the trace reconstruction system 102 to correct all types of errors because there are other error correction techniques that may be used to recover the binary data 208.

Although the implementation discussed herein relates to obtaining binary data 208 from reads of a synthetic DNA strand 200, the trace reconstruction system 102 operates equally well on reads of natural DNA strands. The output from the polynucleotide sequencer 110 is a plurality of noisy reads 202 for both synthetic DNA and natural DNA. Thus, the trace reconstruction system 102 may be used to remove errors from reads generated by the polynucleotide sequencer 110 in implementations that do not involve the use of synthetic DNA to store binary data 208.

Figure 3:
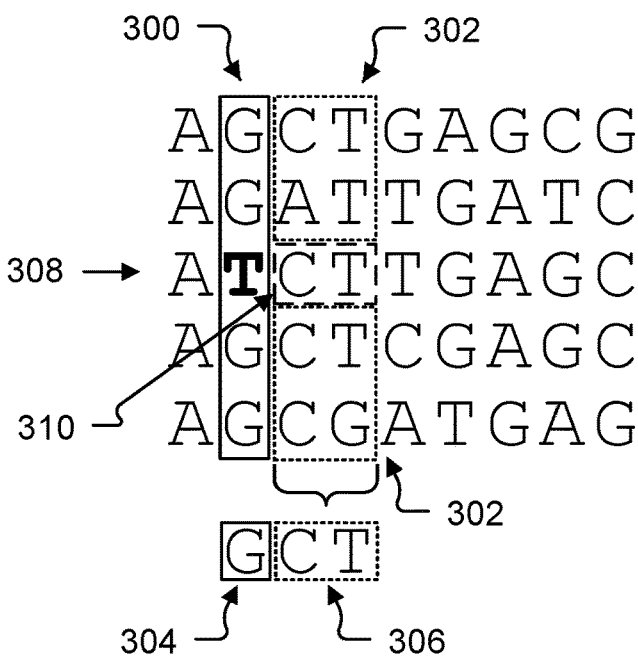
FIG. 3 shows an illustrative representation of a substitution error identified according to the techniques of this disclosure.
Figure 3:
Figure 3:

FIG. 3 shows a technique for identifying a substitution error. The reads may be aligned at a starting position or any other position such as an alignment anchor discussed in greater detail below. The starting position may correspond to the 5' end of the DNA strand that generated the read. In the figures of this disclosure the 5' end is oriented to the left. A position of comparison 300 spanning the reads is represented by the solid rectangular box. The position of comparison 300 may move along the reads from left to right as each position in the reads is analyzed in turn. Immediately following the position of comparison 300 is a look-ahead window 302 represented by two dotted rectangular boxes. The look-ahead window 302 "looks ahead" to the right, or towards the 3' end, of the position of comparison 300. That is, if the read is represented as $Y_j$ and the position of comparison 300 is represented as $p[j]$, then the look-ahead window 302 of length w is the substring consisting of $Y_j[p[j]+1], \ldots Y_j[p[j]+w]$. The look-ahead window 302 may move along the reads as the position of comparison 300 moves. In this example, the length of the look-ahead window 302 is two positions, but it may be longer such as three, four, or more.

A plurality consensus base 304 is the most frequent base call at the position of comparison 300. Here, four of the five reads have G at this position and one read has T. Because G is the most numerous base call, the plurality consensus base 304 is G. In some implementations, the plurality consensus base 304 may be determined by consideration of quality information for the respective base calls at the position of comparison 300. Each base call in the position of comparison 300 may be weighted based on associated quality information. For example, if there is 80% confidence that a given base call is a G then that may count as 0.8 G towards a determination of the plurality consensus base 304 while 30% confidence that a given base call is C will count as 0.3 C towards the determination of the plurality consensus base 304. Thus, the confidence of individual base calls may be considered in identifying the plurality consensus base 304 for a given position of comparison 300. Additionally, or alternatively, all base calls with quality information indicating a confidence in the base call less than a threshold level (e.g., 15%) may be omitted from the determination of the plurality consensus base 304. If two, or more, different base calls are present with equal frequency, the plurality consensus base 304 may be randomly selected from among them.

A read that has a base call at the position of comparison 300 that differs from the plurality consensus base 304 is referred to as a variant read. Thus, for variant read $Y_k$ the base call $Y_k[p[k]]$ does not agree with the plurality consensus base 304. A variant read in this example is the third strand 308. Out of any grouping of reads, when analyzed at a given position of comparison 300, there may be zero, one, or more than one variant reads.

A look-ahead window consensus 306 is determined from the look-ahead window 302 in a similar manner as the plurality consensus base 304. Determination of the look-ahead window consensus 306 may also be influenced by quality information. The look-ahead window consensus 306 may be based on base calls weighted by their respective confidence levels and/or by omitting base calls with confidence levels below a threshold. The look-ahead window consensus 306 is determined by consideration of reads that are not variant reads for the position of comparison 300. Thus, the look-ahead window 302 is shown here as covering the non-variant reads but not covering the variant read 308. In this example, the most common base call in the first position of the look-ahead window 302 is C and the most common base call the second position of the look-ahead window 302 is T. Thus, the look-ahead window consensus 306 is a two-position string of the base calls: CT.

Next, the base calls in the look-ahead window 310 of the variant read (CT) are compared to the look-ahead window consensus 306 (CT). Because they match, the mismatch at the second position in the third read 308 is classified as a substitution. In mathematical notation, if $Y_k[p[k]+1]$, . . . $Y_k[p[k]+w]$ agrees with the look-ahead window consensus, then classify the mismatch in $Y_k$ as a substitution. The plurality consensus base 304 is used as the base call for that position in the consensus output sequence 204.

After the type of error for the variant read is classified, the position of comparison 300 is moved to continue analysis of the reads. The position of comparison 300 is moved one position to the right for each of the reads that are not variant reads. In this example, these are the first, second, fourth, and fifth reads. For variant reads in which the error type is classified as substitution, here that is the third read 308, the position of comparison 300 is also moved one position to the right. Thus, as shown in the lower portion of FIG. 3, the position of comparison 300 is moved one position to the right for all of the reads. The analysis repeats at this new position of comparison 312 and in this iteration the second read 314 is identified as a variant read.

Figure 4:
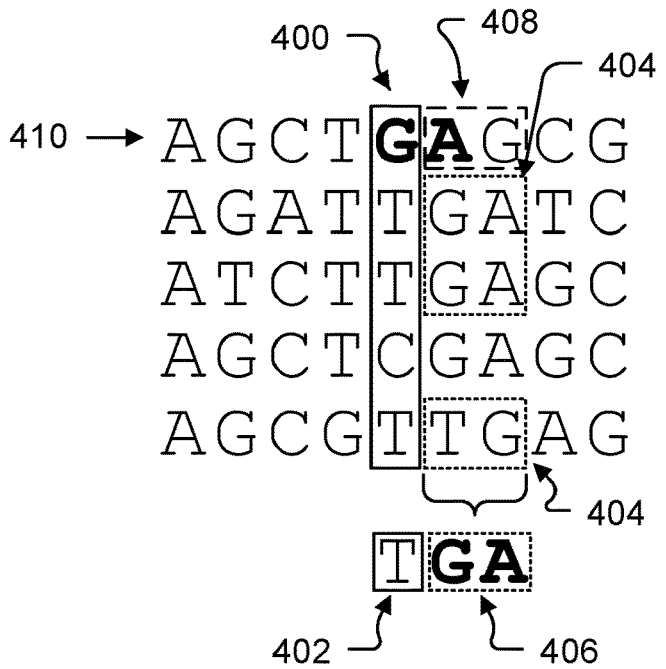
FIG. 4 shows an illustrative representation of a deletion error identified according to the techniques of this disclosure.
Figure 4:
Figure 4:
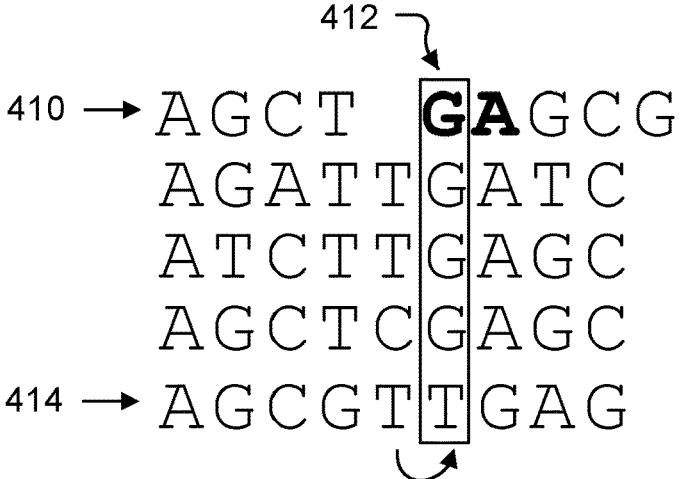

FIG. 4 shows a technique for identifying a deletion error. The position of comparison 400 is again analyzed to determine the most frequent base call at that position. In this example, three of the five strands have the base call T, one strand has the base call G, and one strand has the base call C. Thus, the most common base call is T and the plurality consensus base 402 for this position in the reads is T. The first strand 410 and the fourth strand are identified as variant reads.

Base calls in the look-ahead window 404 for the strands that are not variant reads are compared to determine a look-ahead window consensus 406. In this example, the value of the two base calls in the look-ahead window 404 for the three non-variant reads is GA, GA, and TG. The most common series of base calls is thus GA and this becomes the look-ahead window consensus 406.

The value of the base calls in the look-ahead window 408 (AG) for the first strand 410 is not the same as the look-ahead window consensus 406 (GA). The type of error responsible for the mismatch in the first strand 410 is therefore not classified as a substitution. However, the base calls in the position of comparison 400 and all but the final position of the look-ahead window 404 (GA) match the look-ahead window consensus 406 (GA). Thus, the type of error for this position of the first strand 410 is classified as a deletion. In this example, the length (w) of the look-ahead window 404 is two, so all but the final position of the look-ahead window 404 is w−1 or the first base of the look-ahead window 404. If the look-ahead window 404 has length (w) three, then the first two bases (3-1) of the look-ahead window 404 would be considered when determining if the type of error in the variant read is a deletion. In mathematical notation, if $Y_k[p[k]]$, . . . $Y_k[p[k]+w−1]$ agrees with the look-ahead window consensus, then classify the mismatch in $Y_k$ as a deletion.

After the type of error for the variant read is classified, the position of comparison 400 is moved one position to the right for each of the reads that are not variant reads and for each of the reads for which the error is classified as a substitution. For the first strand 410 in which there is classified as a deletion, the position of comparison 400 is not moved. It remains at the same G located in the fifth position of the first strand 410. The deletion becomes evident as shown in the lower portion of FIG. 4 after realignment of the strands following the differential movement to a new position of comparison 412 for the first strand 410 (i.e., by zero) and for the other strands (i.e., by one). This realignment due to moving to the new position of comparison 412 different amounts based on the classification of the error type keeps the strands in phase improving further analysis farther along the strands. After the new position of comparison 412 is moved (or not depending on the error type) the analysis can repeat, here identifying a mismatch in the fifth strand 414.

Figure 5:
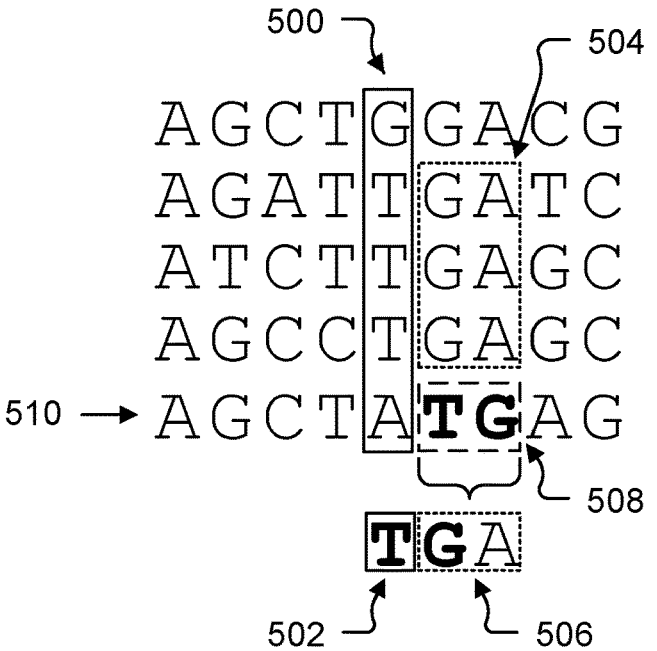
FIG. 5 shows an illustrative representation of an insertion error identified according to the techniques of this disclosure.
Figure 5:
Figure 5:
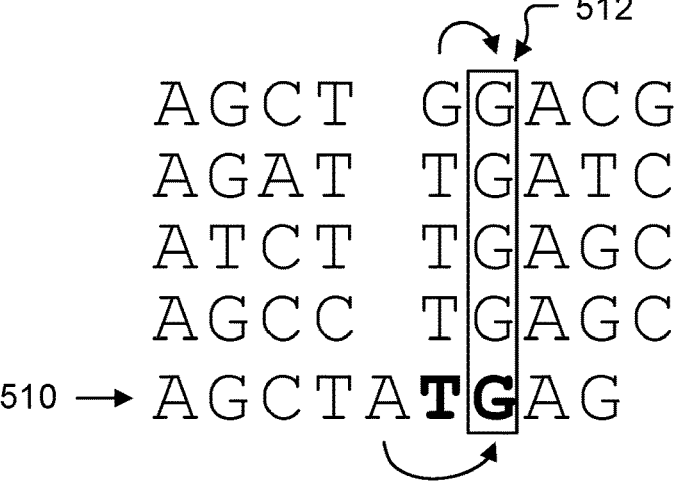

FIG. 5 shows a technique for identifying an insertion error. As discussed above, the three possible error types are substitution, deletion, and insertion. As with identification of substitution and deletion errors, identification of insertion errors begins with analyzing the base calls in a position of comparison 500 to determine a plurality consensus base 502 and analyzing base calls in a look-ahead window 504 to identify a look-ahead window consensus 506. In this example, the plurality consensus base 502 is T. The fifth read 510 is a variant read because it has an A rather than a T at the position of comparison 500. The base calls for the look-ahead window consensus 506 is GA. The base calls in the look-ahead window 508 for the fifth read 510 do not match the look-ahead window consensus 506 so the error type is not classified as a substitution. The base call in the position of comparison 500 and the first base call in the look-ahead window 508 for the variant read (AT) do not match the look-ahead window consensus 506 (GA) so the error type is not classified as a deletion.

However, the base calls in the look-ahead window 508 of the fifth read 510 match the base calls of the plurality consensus base 502 and all but the final base call (i.e., w−1 positions) of the look-ahead window consensus 506 (i.e., both are TG). Thus, the error is classified as insertion of an A at the 5th position of the fifth read 510. In mathematical notation, if $Y_k[p[k]+1]$ agrees with the plurality consensus base 502, and $Y_k[p[k]+2], \ldots Y_k[p[k]+w]$ agrees with the first w−1 coordinates of the look-ahead window consensus 506, then the mismatch in $Y_k$ is classified as an insertion. This insertion error becomes evident as shown in the lower portion of FIG. 5 after realignment of the strands following differential movement of the position of comparison 500 to a new position of comparison 512. The position of comparison 500 is advanced two positions for the read that had the insertion, here that is the fifth read 510. For the other strands, the position of comparison 500 is advanced one position to the new position of comparison 512 for reads that are not variant reads, one position for reads that have substitutions, and zero positions for reads that have deletion errors.

The examples shown in FIGS. 3-5 illustrate analysis of only one type of error each. However, the techniques of this disclosure are equally applicable to groups of reads that have multiple errors in one position of comparison. There may also be multiple error types across a single position of comparison, for example, out of a total of 20 reads (m=20) three reads could have substitutions, one read could have a deletion, and one read could have an insertion.

Figure 6:
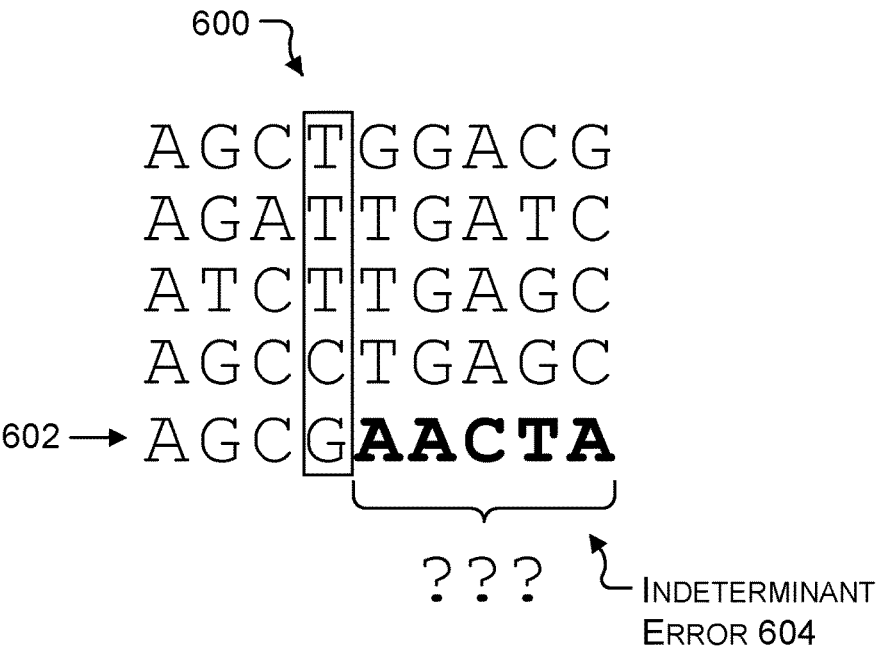
FIG. 6 shows an illustrative representation of an indeterminant error and inactive trace according to the techniques of this disclosure.
Figure 6:
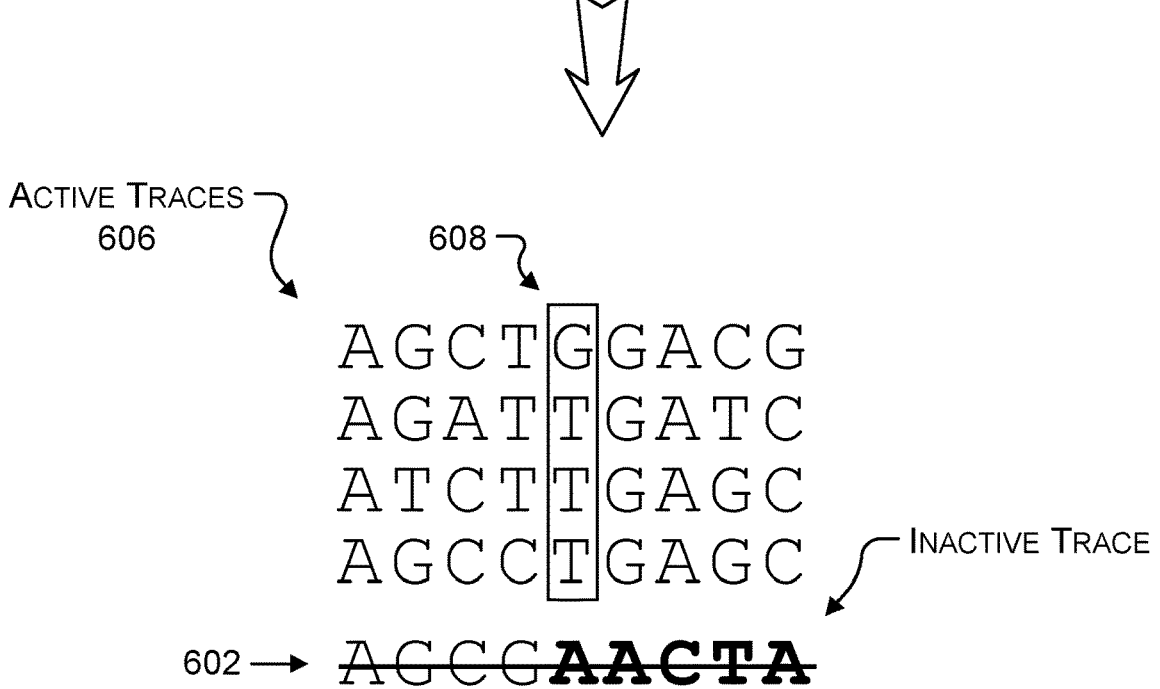

FIG. 6 illustrates a situation in which it is not possible to identify the type of error. A read may have a base call in the position of comparison that does not match the plurality consensus base call, thus it is a variant read, but the base calls in the position of comparison and the look-ahead window may not exhibit any of the relationships classified as substitution, deletion, or insertion. This is an error that cannot be classified according to the techniques described above, and thus, is referred to as an "indeterminant error" 604. Even if other techniques are used for identifying the type of error besides those described in this disclosure, an error or a failure to match with the plurality consensus base call that cannot be resolved to a specific type of error can be classified as an indeterminate error.

Use of the techniques shown in FIGS. 3-5 cannot classify the base calls at the location of the indeterminant error 604 in the fifth read 602 as a substitution, an insertion, or a deletion. The position of comparison 600 immediately prior to the location of the indeterminant error 604 is the last position before the indeterminant error 604.

One way of handling reads that have indeterminant errors is to discard the read from further processing. Thus, if a read has an error and it cannot be resolved to a single error type, that read is omitted from further analysis. If the read 602 is discarded, it may be indicated as an "inactive trace" because the read 602 does not contribute any information to trace reconstruction. Once the read 602 is identified as an inactive trace, the consensus output sequence is generated from the remaining active traces 606. The active traces 606 may be all of the other reads from the same cluster or may be fewer than all the other reads if some are discarded for also including indeterminant errors, for low confidence levels, or otherwise.

However, completely discarding a read also discards useful information that may be contained in portions of the read that do not have indeterminant errors. For some sequencing technologies, such as Nanopore sequencing, discarding every read that has an indeterminant error can reduce the number of recovered clusters significantly, because this may even leave so few reads remaining that is not possible to perform trace reconstruction.

Another way of handling ambiguous errors is to use a bias or tiebreaker in order to force a classification. The bias may be based on an error profile of the polynucleotide sequencer used to generate the reads. For example, if the polynucleotide sequencer is known to generate substitution errors much more frequently than either deletion or insertion errors, all ambiguous errors could be classified as substitutions. If an error can be identified as one of two possible error types, the relative frequency of those error types for the polynucleotide sequencer technology may be used to choose between them. For example, if an error has been identified as either a deletion or insertion (but not a substitution) and the polynucleotide sequencer makes 80% substitution errors, 15% deletion errors, and 5% insertion errors, that error may be classified as a deletion error because deletion errors are more likely than insertion errors in this example. However, this may decrease the reliability of the consensus output sequence because base calls that are likely incorrect may be included in the calculation of the consensus base call.

Additionally, or alternatively, the quality information of individual base calls may be used to classify ambiguous errors. In one implementation, when an error is unable to be resolved to a single error type, all base calls in the position of comparison and the look-ahead window with quality information indicating a base call confidence of less than a threshold level may be omitted from the determination of the plurality consensus base and the look-ahead window consensus. Thus, the consensus base calls for the relevant positions are determined on the most reliable base calls from the multiple reads. Ignoring the low-confidence base calls may lead to the techniques described above being able to resolve the error to a single error type. If, however, the confidence level is low for most of the base calls or even if the confidence level is consistent then selecting specific base calls based on confidence levels may not yield accurate results.

Figure 7:
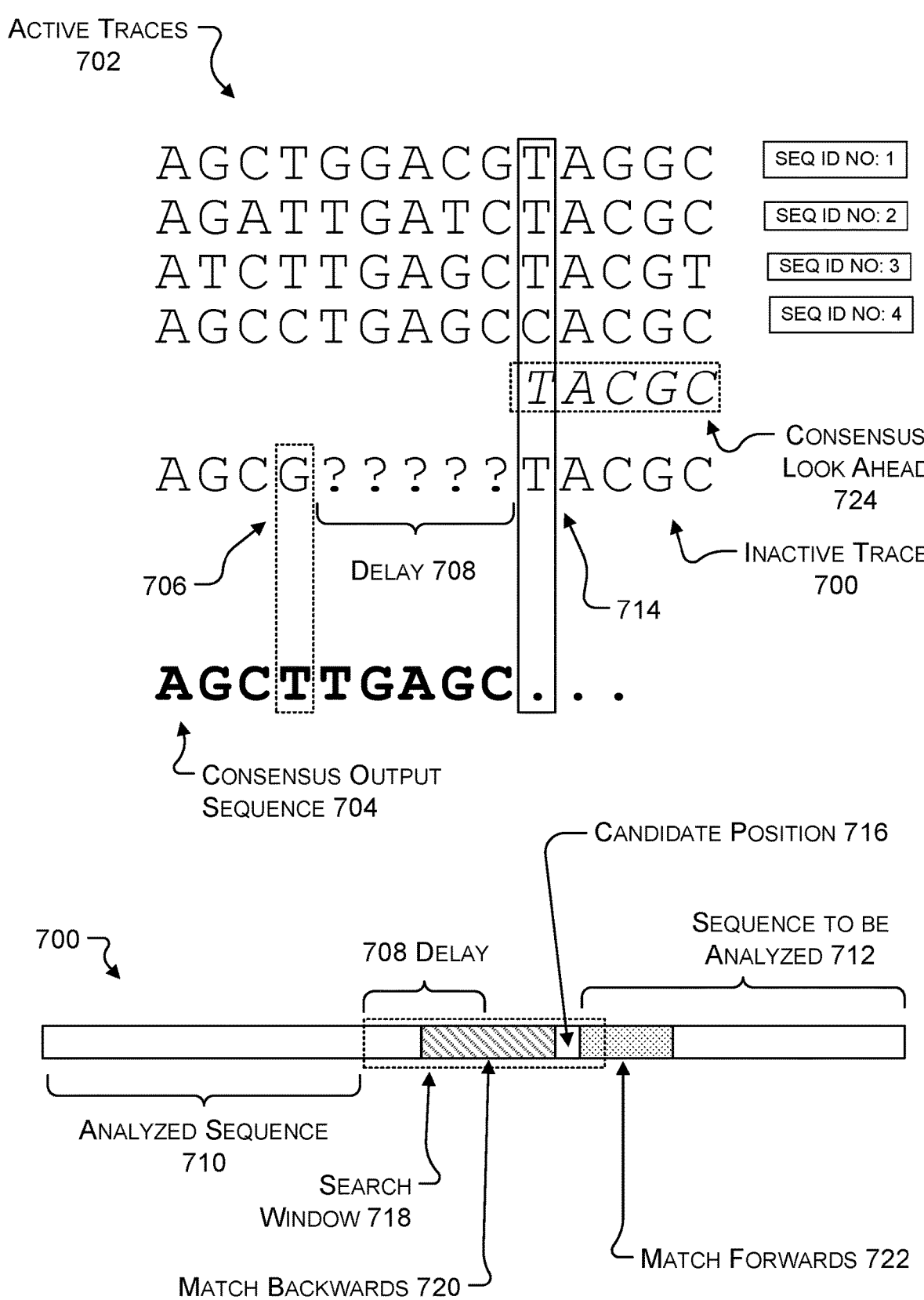
FIG. 7 shows an illustrative representation of introducing a delay into an inactive trace and locating a candidate position within the inactive trace.

FIG. 7 shows a technique for skipping over a portion of an inactive trace 700 that contains an indeterminant error to search for a match with the active traces 702 at a later position located further along the inactive trace 700. The inactive trace 700 may be labeled as an inactive trace due to identification of an indeterminant error as shown in FIG. 6. The strings of base calls represented by each of the reads in a cluster may be represented as $Y_1, Y_2, \ldots, Y_m$. The value of m can vary based on the sequencing technology and the depth of coverage. For example, with Nanopore sequencing m may be about 10-100. The inactive trace 700 can be represented as $Y_j$.

A consensus output sequence 704 can be generated from the active traces 702 and portions of the inactive trace 700. The consensus output sequence 704 may be represented as $\hat{X}$ which is the best estimate for X the sequence for the polynucleotide provided to the oligonucleotide sequencer. As discussed previously, the consensus output sequence 704 identifies the plurality consensus base call while accounting for insertions, deletions, and substitutions to maintain alignment of the reads relative to one another.

The position 706 is the position in the inactive trace 700 that was estimated when the read last became inactive. This may be the position of comparison 600 shown in FIG. 6. This position can be represented as i*. Then p*[j] is the position in $Y_j$ that was the position of comparison when the read last became inactive. A delay 708 of several positions (e.g., 5-10) is introduced in the inactive trace 700 before resuming evaluation of the base calls in the inactive trace 700. The delay 708 is a portion of the inactive trace 700 that will be maintained as inactive regardless of any potential matches in this area. The last "good" position in the inactive trace 700 is identified at position 706, but it is not known how many positions are affected by the indeterminant error. With sequences that include bursty errors such as those from Nanopore sequencing, it is likely that there are several positions adjacent or close to one another that have mismatches which will not be able to be classified as insertions, deletions, or substitutions. Introducing the delay 708 reduces the likelihood that the inactive trace 700 will be returned to active status at a position where there is a mismatch.

The schematic representation of the inactive trace 700 at the bottom of FIG. 7 shows one illustrative arrangement of how the inactive trace 700 can be evaluated to identify a matching sequence. When an indeterminant error is identified there is likely some portion of the inactive trace 700 that has already been analyzed extensively and used to develop the consensus output sequence 704. This section of the inactive trace 700 is indicated as the analyzed sequence 710. This is followed by the delay 708 and then past the delay 708 is a portion of the inactive trace 700 that has the sequence which is yet to be analyzed 712. Once it is identified how far past the delay 708 the inactive trace 700 can be reactivated, trace reconstruction may be resumed.

There is a position of comparison 714 following the delay 708 that may be represented as i. To determine if this position of comparison 714 is within the delay 708 region, i is compared to i*: if i−i*≤delay then the inactive trace 700 is kept as inactive, but if i−i*>delay then the inactive trace 700 is evaluated at position i as described below.

For alignments of the reads for which the consensus output sequence 704 has not yet been calculated, a consensus look ahead sequence 724 can be created from the active traces 702. The consensus look ahead sequence 724 may be created the same way as the look-ahead window described earlier by taking the plurality consensus vote of the active traces 702 at a position of comparison. This technique simply uses the plurality consensus base call at each position as the base call for the consensus sequence. If there is an equal number of base calls (e.g., 5 T's and 5 C's) then ties are broken arbitrarily. However, unlike the look-head window, the consensus look ahead sequence 724 is not limited to a window of two or three positions.

Once past the delay 708 region, a candidate position 716 is sought. The candidate position 716 is a single position in the inactive trace 700 which can be aligned with the active traces 702 and used for continuing with determination of the consensus output sequence 704. The candidate position 716 can be represented as k. The candidate position 716 may immediately follow the delay 708 at the position of comparison 714 or it may be located somewhere farther past the end of the delay 708.

If insertions and deletions occurred with equal frequency from position 706 to the candidate position 716, then the position at which the inactive trace 700 once again can be aligned with the active traces 702 would be at or near the position of comparison 714. This position of comparison 714 may be represented as $k_0$. It can be calculated by adding the difference i−i* between the candidate position i and the position i* to the position of comparison when the read last became inactive. Thus, $k_0 := p*[j]+(i−i*)$. However, there may be an unequal number of insertions and deletions from position 706 to the candidate position 716. Accordingly, a search window 718 is used to evaluate multiple possible locations for a match between a subsequence of the inactive trace 700 and the active traces 702 in a region around $k_0$.

The search window 718 may include a search backwards window (sbw) before $k_0$, a search forwards window (sfw) past $k_0$, as well as $k_0$ itself. Thus, the search window 718 is a range of possible positions for k in the neighborhood of $k_0$. The multiple possibilities fork may be represented as $k \in \{k_0−sbw, k_0−sbw+1, \ldots, k_0−1, k_0, k_0+1, \ldots, k_0+sfw−1, k_0+sfw\}$ Each possibility for k can be evaluated to determine if there is a subsequence of the inactive trace 700 that matches the active traces 702. A larger search window 718 resulting from larger values for sbw and sfw makes it more likely to find a match but also increases the possibility of returning a false positive result. The size for the search window 718 may be determined experimentally. The total length of the search window 718 is sbw+sfw+1. Thus, if sbw and sfw are both 5 positions long, then the length of the search window 718 will be 11 positions. The sbw and sfw may be the same length as each other or different lengths.

Subsequences of the inactive trace 700 within the search window 718 are compared a comparison sequence Z to determine if there is a match. The comparison sequence Z includes the base call at position i in $\hat{X}$ and may include one or both of a match-backwards (mb) 720 region and a match-forwards (mf) 722 region.

The match-backwards 720 region is located before position i and aligns with portions of the consensus output sequence 704. A length of the match-backwards 720 sequence may be determined experimentally and can range from, for example, 0-10 positions. Thus, the match-backwards 720 sequence may be omitted. The match-backwards 720 sequence may also overlap with the delay 708. At the positions represented by the delay 708, the consensus output sequence 704 is determined by the active traces 702 without using the base calls from the inactive trace 700 at the location of the delay 708.

The first mb+1 positions of Z are $\hat{X}[i−mb]$, $\hat{X}[i−mb+1], \ldots \hat{X}[i−1], \hat{X}[i]$. Thus, this represents the portion of the comparison sequence Z that is the same as the consensus output sequence 704 at the positions being evaluated. Even if the length of mb is 0, $\hat{X}[i]$ is included in Z.

The match-forwards 722 sequence extends past position i and as such there is no consensus output sequence 704 at corresponding positions. Thus, for the purposes of comparing to the sequence in the inactive trace 700, the consensus look ahead sequence 724 sequence from the active traces 702 is used. The length of the match-forwards 722 sequence can be, for example, 0-10 positions. Thus, if mf=0 then the match-forwards 722 sequence is not used. Although the match-backwards 720 sequence and the match-forwards 722 sequence are both compared to a consensus sequence generated from the active traces 702, each is compared to different consensus sequences. The match-backwards 720 sequence is compared to $\hat{X}$ the consensus output sequence 704 while the match-forwards 722 sequence is compared to the consensus look ahead sequence 724.

The subsequence of the inactive trace 700 that is compared to Z has a length of mb+mf+1 which is the same length as Z. Thus, the matching is performed between two strings of equal length. Recall that the inactive trace 700 may be represented as $Y_j$ and thus, the subsequence of the inactive trace 700 that is compared to Z can be represented as $$Y_j^k$$

because its location is based on the location of k. Specifically, $$Y_j^k$$

can be defined as $Y_j[k-mb]$, $Y_j[k-mb+-1]$, . . . , $Y_j[k-1]$, $Y_j[k]$, $Y_j[k+1]$, . . . , $Y_j[k+mf-1]$, $Y_j[k+mf]$.

With these definitions of $$Z \text{ and } Y_j^k$$

it is possible to make comparisons for each $k \in \{k_0-sbw, k_0-sbw+1, \ldots, k_0-1, k_0, k_0+1, \ldots, k_0+sfw-1, k_0+sfw\}$ to determine if there is any candidate position 716 that represents a match. A match may be no more than a distance threshold (dt) in the edit distance between the two strings. If dt=0 then only exact matches will be considered as matching. The number of comparisons may be the same as the length of the search window 718. Thus, if the search window is 12 positions long, a sliding window of 12 positions is moved along the search window 718 and compared to the corresponding base call sequences in Z.

If none of the candidate positions 716 within the search window 718 are associated with a $$Y_j^k$$

subsequence that matches the corresponding Z subsequence, then the inactive trace 700 may be kept as inactive. The entire read may be discarded or only the portion of the read before the indeterminant error (i.e., the analyzed sequence 710) may be used.

If there a candidate position 716 within the search window that is associated with a $$Y_j^k$$

subsequence that matches the corresponding Z subsequence, the position of comparison for trace reconstruction may be set as the position immediately following the candidate position 716. The location of the position of comparison may be calculated as p[i]:=k+1. The inactive trace 700 may again be designated as an active trace and trace reconstruction including this read can proceed forward from the position of comparison.

There may be multiple candidate positions 716, multiple locations for k, at which a match is found. If so, one of the candidate positions 716 is selected to be used as the location for restarting trace reconstruction. One way is to select the position closest to $k_0$. Alternatively, the position farthest from $k_0$ could be selected or the selection could be random.

A given read may have more than one indeterminant error and the process of identifying the indeterminant error followed by finding a candidate position 716 to restart trace reconstruction can be repeated multiple times in a single read. Furthermore, a cluster of reads which may include many tens of sequences can have multiple reads that include an indeterminant error. Thus, this technique can be used on more than one, including all, of the reads in a cluster.

Because at various positions for i different ones of the multiple reads may be active or inactive, the set of reads that makes up the active traces 702 can be different at different alignment locations.

Figure 8:
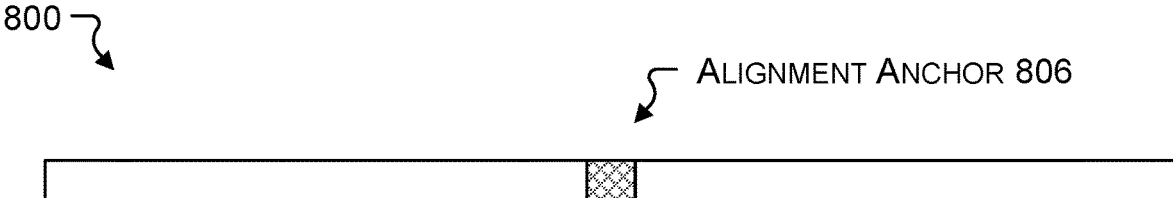
FIG. 8 shows placement positions for alignment anchors within a read.
Figure 8:
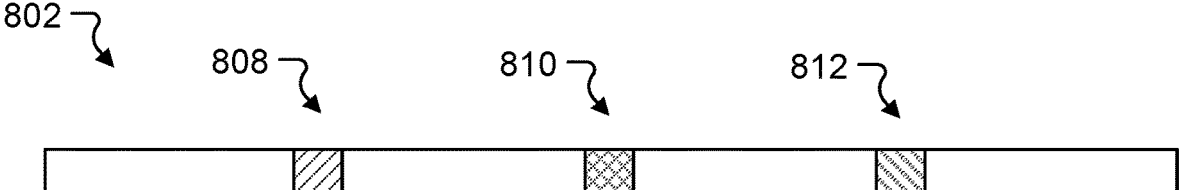
Figure 8:
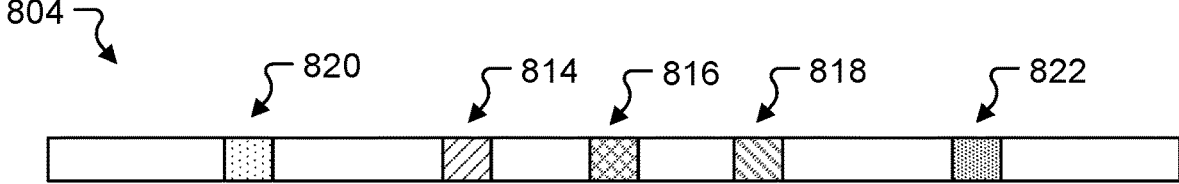

FIG. 8 is a schematic diagram of several DNA strands 800, 802, 804 indicating locations of alignment anchors. Alignment anchors provide reference locations, in addition to the start and the end of the reads, that can align multiple noisy reads, and thus, assist with constructing the consensus output sequence.

Generally, the accuracy of a consensus output sequence is more accurate towards the beginning or end of a read where there is higher confidence in the strands being in correct alignment with each other. Without being bound by theory, it is possible that any errors may accumulate and cause further errors in analysis of subsequent positions along the reads. For example, if a deletion error is incorrectly identified as a substitution error, the remaining base calls in that read may be out of phase and negatively impact the accuracy of subsequent consensus base calls. One way of minimizing this effect is to use the first half of the "forward" analysis and the first half of the "reverse" analysis. Say, for example, that the length of the read to be analyzed is 200 positions. A left-to-right analysis may be performed that provides a consensus output sequence for positions 1-100. A right-to-left analysis may also be performed that provides a consensus output for positions 101-200. Both analyses may be performed in parallel. The resulting consensus output sequence provides a base call for all of positions 1-200 by combining the left-to-right analysis and the right-to-left analysis. This is referred to as a combined consensus output sequence.

Because with combined consensus output sequences are least reliable further from the ends of a read, one arrangement is to add at the alignment anchor 806 at the center of the DNA strand 800. This provides a position to realign the reads at the location where the relative alignment to each other is least reliable. The markers provide an "anchor" for the consensus alignment to reset and begin again without the influence of previously accumulated errors.

The alignment anchors function as markers of location and should be recognizable in each read even in the presence of noise and errors created by sequencing. The alignment anchors may be relatively short sequences of, for example, 4-8 positions. Selection of the base sequence in an alignment anchor and the length of the alignment anchor may be arbitrary. Any sequence that is consistent across multiple DNA strands that cluster together can function as an alignment anchor. Because the alignment anchors use some number of bases, this comes at the cost of reducing the number of bases in the DNA strands that are available for storing digital information. However, including alignment anchors in the DNA strands may make it possible for trace reconstruction to generate accurate consensus output sequences with lower levels of coverage thereby reducing the total amount of sequencing needed to recover the information stored in the DNA.

In an implementation, the sequence of the alignment anchors is created to avoid repeating bases and to avoid internal alignments. Because the alignment anchors are used to align multiple reads, reducing the possibility of a misalignment between alignment anchor sequences in two different reads may be beneficial. For example, ACGT is a sequence that does not have any repeating bases and does not have any internal alignments. But ACGACG could form partial alignments with itself if the first ACG in one read aligned with the last ACG in a different read. Misalignments may occur, for example, if there is an error in the base calls for positions within an alignment anchor or the sequence of the read adjacent to an alignment anchor is the same as part of the alignment anchor.

One or more alignment anchors may be included in the polynucleotide sequence of a DNA strand. There are multiple possible arrangements for the alignment anchors within a DNA strand. One arrangement is to place an alignment anchor 806 centered in the middle of a DNA strand 800. Placing the alignment anchor 806 in the center of the DNA strand 800 will of course lead to the alignment anchor sequence being at or close to the middle of the corresponding read. For example, the alignment anchor 806 may be located between 40%-60%, 45%-55%, 49%-51%, or 50% of the distance from the beginning of DNA strand 800 to the end of the DNA strand 800.

DNA strands 802 and 804 show examples of multiple alignment anchors. If multiple alignment anchors are used, they may be arranged in various ways. DNA strand 802 illustrates an example in which alignment anchors 808, 810, and 812 are equally spaced. Thus, the number of positions between the start of the DNA strand 802 and alignment anchor 808, between alignment anchor 808 and alignment anchor 810, between alignment anchor 810 and alignment anchor 812, and between alignment anchor 812 and the end of the DNA strand are all substantially the same. The alignment anchors can act as additional "ends" to the DNA strand 802 for the purpose of aligning multiple reads. Thus, if DNA strand 802 is 200 bp long, rather than creating one right-to-left consensus output sequence of 100 positions and one left-to-right consensus output sequence of 100 positions, the alignment anchors 806, 810, and 812 divide the DNA strand 802 into four regions of approximately 50 bp each. Thus, the length of sequencing before an alignment point is reached is shortened from 200 bp to about 50 bp and the opportunity for mistaken base calls to place one of the reads out of phase with the others is also decreased.

In a different arrangement illustrated by DNA strand 804, the spacing of alignment anchors may be biased towards the center of the DNA strand. Thus, the alignment anchors 814, 816, and 818 near the center of the DNA strand 804 are located closer together than the alignment anchors 820 and 822 which are farther away from the center. Also, alignment anchors 820 and 822 may be yet farther away from the respective ends of the DNA strand 804. Each alignment marker used together should be unique so that it can be differentiated from other markers. Thus, anchors 814-822 will each have different sequences. The length of the individual anchors may also be different.

Figure 9:
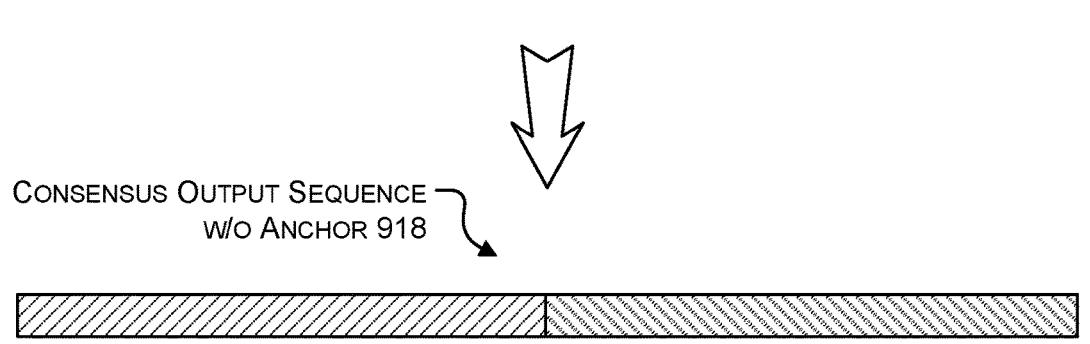
FIG. 9 shows generating partial consensus sequences from segments of a read divided by an alignment anchor.

FIG. 9 uses schematic diagrams of reads to illustrate how partial consensus sequences generated from portions of reads divided by alignment anchors can be joined to create a full consensus output sequence. The read 900 illustrated in FIG. 9 may, for example, be generated from the DNA strand 800 shown in FIG. 8. The alignment anchor 902 may be located in the middle of the read 900 about 50% of the way between the left end and the right and of the read 900. Even if the alignment anchor 902 is located exactly 50% along the length of the DNA strand, insertions and/or deletions introduced during sequencing may shift the position of the alignment anchor 902 in the read so that it is no longer exactly in the middle. Thus, alignment anchor 902 divides the read 900 into two portions of roughly equal length.

Because the sequence of the alignment anchor 902 is known (assuming no errors in this portion of the read 900), a search for that known sequence (e.g., AGCT) may identify one or more matches throughout the read 900. The placement of the alignment anchor 902 is also known, so any matches that are not within a threshold distance from the middle of the read 900 may be ignored. Thus, the location of the alignment anchor 902 can be identified in the read 900 and in other reads in the same cluster.

If the read 900 is 180 positions long and the alignment anchor 902 is four positions long and located exactly in the middle, then the left subsequence of read 900 located to the left of the alignment anchor 902 will be 88 positions long and the right subsequence located to the right of the alignment anchor 902 will also be 88 positions long. The left subsequence may be analyzed by forward and reverse analysis to generate a left-to-right consensus output sequence 904 and a right-to-left consensus output sequence 906. Similarly, the right subsequence may be analyzed to generate the consensus output sequences 908 and 910.

As discussed above, only the first half of each of these four consensus output sequences 904-910 may be used to minimize errors introduced by accumulative phase shifts caused by insertions and deletions resulting from sequencing. In this implementation, only 44 positions would be analyzed before switching to the consensus output sequence running the opposite direction. Alternatively, more than half of each of the respective consensus output sequences may be used so that there is some level of overlap near the middle of the subsequences. In the area of overlap, base calls from both the left-to-right and the right-to-left consensus output sequences may be used to determine the consensus output base call that will be assigned to a position.

Combination of the left-to-right consensus output sequence 904 and the right-to-left consensus output sequence 906 may generate a partial consensus sequence 912 for the left half of the read 900. Similarly, the consensus output sequences 908 and 910 may be combined in any suitable manner to generate the partial consensus sequence 914 for the right half of the read 900. The partial consensus sequence 912 may be aligned with the partial consensus sequence 914 by reference to the alignment anchor 902.

Once aligned, the partial consensus sequence 912 and the partial consensus sequence 914 may be joined using the alignment anchor 902 to create a single joined consensus sequence 916. The joined consensus sequence 916 represents a consensus output sequence for the read 900 that was developed from the forward and the reverse consensus output sequences 904-910. This contrasts with an implementation that does not use alignment anchors in which the consensus output sequence for the read 900 would be created from only one forward and one reverse consensus output sequences.

Because the alignment anchor 902 does not encode digital information like other portions of the read 900, the base calls corresponding to the alignment anchor 902 may be removed to create the consensus output sequence without the alignment anchor 918. The consensus output sequence without the alignment anchor 918 represents a string of base calls that can be decoded to recover the digital information contained in the read 900.

Figure 10:
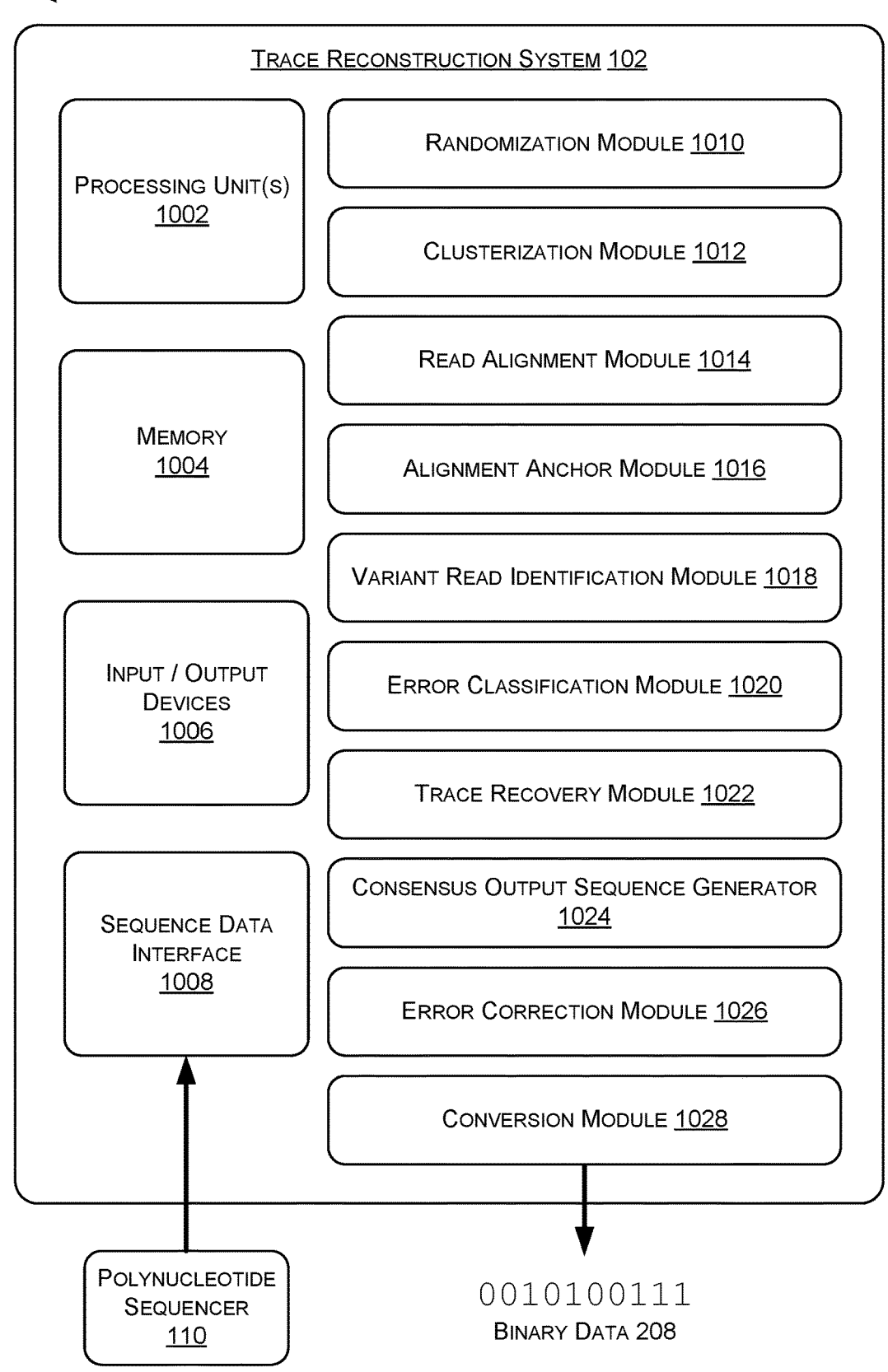
FIG. 10 shows a block diagram of an illustrative trace reconstruction system.

FIG. 10 shows an illustrative block diagram 1000 of the trace reconstruction system 102 shown in FIG. 1. Recall that the trace reconstruction system 102 may be implemented in whole or in part in any of the computing device 112, the polynucleotide sequencer 110, and the servers 114. Thus, the trace reconstruction system 102 may be implemented in a system that contains one or more processing unit(s) 1002 and memory 1004, both of which may be distributed across one or more physical or logical locations. The processing unit(s) 1002 may include any combination of central processing units (CPUs), graphical processing units (GPUs), single core processors, multi-core processors, application-specific integrated circuits (ASICs), programmable circuits such as Field Programmable Gate Arrays (FPGA), and the like. One or more of the processing unit(s) 1002 may be implemented in software and/or firmware in addition to hardware implementations. Software or firmware implementations of the processing unit(s) 1002 may include computer- or machine-executable instructions written in any suitable programming language to perform the various functions described. Software implementations of the processing unit(s) 1002 may be stored in whole or part in the memory 1004.

Alternatively, or additionally, the functionality of the trace reconstruction system 102 can be performed, at least in part, by one or more hardware logic components. For example, and without limitation, illustrative types of hardware logic components that can be used include Field-programmable Gate Arrays (FPGAs), Application-specific Integrated Circuits (ASICs), Application-specific Standard Products (AS-SPs), System-on-a-chip systems (SOCs), Complex Programmable Logic Devices (CPLDs), etc. Implementation as hardware logic components may be particularly suited for portions of the trace reconstruction system 102 that are included as on-board portions of the polynucleotide sequencer 110.

The trace reconstruction system 102 may include one or more input/output devices 1006 such as a keyboard, a pointing device, a touchscreen, a microphone, a camera, a display, a speaker, a printer, and the like.

Memory 1004 of the trace reconstruction system 102 may include removable storage, non-removable storage, local storage, and/or remote storage to provide storage of computer-readable instructions, data structures, program modules, and other data. The memory 1004 may be implemented as computer-readable media. Computer-readable media includes at least two types of media: computer-readable storage media and communications media. Computer-readable storage media includes volatile and non-volatile, removable and non-removable media implemented in any method or technology for storage of information such as computer-readable instructions, data structures, program modules, or other data. Computer-readable storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other non-transmission medium that can be used to store information for access by a computing device.

In contrast, communications media may embody computer-readable instructions, data structures, program modules, or other data in a modulated data signal, such as a carrier wave, or other transmission mechanism. As defined herein, computer-readable storage media and communications media are mutually exclusive.

The trace reconstruction system 102 may be connected to one or more polynucleotide sequencers 110 through a direct connection and/or a network connection by a sequence data interface 1008. The direct connection may be implemented as a wired connection, a wireless connection, or both. The network connection may travel across the network 116. The sequence data interface 1008 receives one or more reads from the polynucleotide sequencer 110.

The trace reconstruction system 102 includes multiple modules that may be implemented as instructions stored in the memory 1004 for execution by processing unit(s) 1002 and/or implemented, in whole or in part, by one or more hardware logic components or firmware.

A randomization module 1010 randomizes input digital data before encoding it in DNA with oligonucleotide synthesizer 104. The randomization module 1010 may create a random, more accurately pseudo-random, string from the input digital data by taking the exclusive-or (XOR) of the input string and a random string. The random string may be generated using a seeded pseudo-random generator based on a function and a seed. Such randomization of the input digital data increases randomness in synthetic DNA strands 200 which results in the noisy reads 202 coming from a polynucleotide sequencer 110 themselves having a pseudo-random sequence of A, G, C, and T. The randomness facilitates decoding (i.e., clustering and trace reconstruction).

A clusterization module 1012 clusters a subset of the plurality of reads based on a likelihood of the subset of the plurality of reads being derived from the same DNA strand. Data received at the sequence data interface 1008 from the polynucleotide sequencer 110 may contain a set of reads generated from each DNA strand provided to the polynucleotide sequencer 110. Although there may be errors in many of the reads, the reads from the same DNA strand are generally more similar to each other than they are to reads from a different DNA strand. Further analysis would be hampered if the set of reads to be analyzed includes reads of different DNA strands. Thus, clustering may be performed in order to limit the data for further analysis to a subset of the reads that are believed to represent the same DNA strand. A poorly formed cluster may be "poorly" formed due to over or under inclusion. An overly inclusive, poorly formed cluster is one that groups reads of more than one strand in a single cluster. An underinclusive, poorly formed cluster is one of multiple clusters that should be grouped into a single large cluster but instead are divided into multiple smaller clusters. The clusterization module 1012 can use any suitable clustering technique such as connectivity-based clustering (e.g., hierarchical clustering), centroid-based clustering (e.g., k-means clustering), distribution-based clustering (e.g., Gaussian mixture models), density-based clustering (e.g., density-based spatial clustering of applications with noise (DBSCAN)), etc. The trace reconstruction system 102 may analyze one or more, including all, of the clusters derived from the data output by the polynucleotide sequencer 110. As mentioned above, the number of reads in a cluster may depend on the depth of sequencing. With Nanopore sequencing, there may be between about 10 to 100 reads per cluster.

A read alignment module 1014 aligns the plurality of reads at a position of comparison spanning the plurality of reads. Initially, the left ends of the reads (corresponding to the 5' ends of the DNA strands) may be aligned. This first position in the reads may be used as the initial position of comparison. As analysis proceeds, the read alignment module 1014 moves the position of comparison along each read a number of positions based on identified error types.

The read alignment module 1014 advances the position of comparison by one position for reads that have the plurality consensus base call at the position of comparison, by one position for a variant read if the error type is classified as substitution, by zero positions for a variant read if the error type is classified as deletion, or by two positions for a variant read if the error type is classified as insertion.

The read alignment module 1014 may also generate a "reverse" alignment that begins with the reads aligned at the right end (corresponding to the 3' ends of the DNA strands).

Analysis then proceeds in an identical manner except that movement to the "right" becomes movement to the left. The consensus output sequence 204 is potentially different for the same set of reads when analyzed from left to right as compared to right to left.

Generally, the accuracy of a consensus output sequence 204 is more accurate towards the beginning of the reads where there is higher confidence in the alignment being correct. Without being bound by theory, it is possible that any errors may accumulate and cause further errors in analysis of subsequent positions along the reads. For example, if a deletion error is incorrectly identified as a substitution error, the remaining base calls in that read may be out of phase and negatively impact the accuracy of subsequent error identification. One way of minimizing this effect is to use the first half of the "forward" analysis and the first half of the "reverse" analysis. Say, for example, that the length of the reads to be analyzed is 100 positions. A left-to-right analysis may be performed that provides a consensus output sequence 204 for the first 50 positions. A right-to-left analysis may be performed that provides a consensus output sequence 204 for the last 50 positions. Both analyses may be performed in parallel. The resulting consensus output sequence 204 is a combination of the 50 base pairs identified by the left-to-right analysis and the 50 base pairs identified by the right-to-left analysis. This is referred to as a combined consensus output sequence.

An alignment anchor module 1016 functions by identifying locations of alignment at locations other than the ends of the reads when an alignment anchor sequence is present. When alignment anchors are present, the alignment anchor module 1016 may function together with the read alignment module 1014 to create alignments of segments of reads between one of the ends of a read and an alignment anchor as well as between two alignment anchors if present. The alignment anchor module 1016 can identify an alignment anchor sequence that is present in a read. The alignment anchor sequence is a predetermined sequence such as illustrated in FIGS. 8 and 9. The alignment anchor sequence may be a sequence that is 3-8 bp. In some implementations, alignment anchor sequences may be 4-6 bp long. The alignment anchor sequence may be an arbitrary sequence that is included by design in DNA strands synthesized by the oligonucleotide synthesizer 104. Thus, a few nucleotide bases in the DNA strands are not used to encode digital information but instead are used to insert a known sequence—the alignment anchor sequence. To reduce the probability of misalignment between two alignment anchor sequences, the sequence used as the alignment anchor sequence may be designed without repeating nucleotides and so that it will not align with itself. For example, the sequence "AGCT" may be a suitable sequence for an alignment anchor whereas the sequences "ACACAC" and "TTGG" would be more likely to misalign.

Once alignment anchors are identified and the reads aligned at the alignment anchors, the alignment anchor module 1016 may also divide the read into multiple sub-reads such as a first sub-read and a second sub-read. If there is only one alignment anchor sequence in the read, then the first sub-read may extend from the beginning of the read (e.g., 5'-end) to the alignment anchor sequence and the second sub-read may extend from the alignment anchor sequence to the end of the read (e.g., the 3'-end). The alignment anchor module 1016 may do this for each of the reads under analysis, creating a third, fourth, etc., sub-reads.

The read alignment module 1014 may then align the sub-reads in a similar manner as it aligns entire reads except that the alignment is not based only on the end of the reads but also on the alignment anchors that divide the reads. Thus, the read alignment module 1014 can align the first subsequence from the first half of a first read with a third subsequence that is from the first half of a second read. The second half of the first read represented by the second subsequence can also be aligned with a fourth subsequence that represents the second half of the second read. Thus, instead of aligning the entirety of the first read and the second read, the subsequences of the reads are aligned. Of course, in many implementations more than two reads will be aligned.

Because the subsequences are shorter than the entire reads the effects of accumulated mistakes in generation of the consensus output sequence are reduced. There is a smaller number of positions over which errors may shift one of the reads out of phase with the other reads. If errors did accumulate or a read was out of phase with the other reads in the same cluster, the alignment would be "reset" at the alignment anchor sequence. The sub-reads may be aligned in both forwards and reverse orientations as described above for entire reads and as shown in FIG. 9. Thus, each alignment of subsequences (e.g., the first subsequence, second subsequence, third subsequence, and fourth subsequence from the above example) may be analyzed in the same way as alignments of entire sequences.

A variant read identification module 1018 determines a plurality consensus base call at the position of comparison and labels a read that has a different base call at the position of comparison as a variant read. In some implementations, the variant read identification module 1018 may use an error profile associated with the polynucleotide sequencer 110 as discussed above to determine the plurality consensus base call. The variant read identification module 1018 may flag or otherwise identify every read that is a variant read for a given position of comparison. This flag will then identify that read as one that should be identified for determination of an error type. With each movement of the position of comparison, the identity of which reads are variant reads and which are not variant reads changes.

An error classification module 1020 classifies an error type for variant reads as substitution, deletion, or insertion. If an error cannot be uniquely classified, the error classification module 1020 may indicate that the type of error is indeterminate or that the error type is limited to one of two possibilities. Classification of an error by the error classification module 1020 may be based in part on comparison of a consensus string of base calls in a look-ahead window of a subset of the plurality of reads having the plurality consensus base call at the position of comparison (i.e., the non-variant reads) and base calls in the variant read. Variant reads other than the one being analyzed at a given iteration are not used when determining an error type. If the error classification module 1020 classifies an error in a read as an indeterminant error, the variant read identification module 1018 may label the read as an inactive trace.

As described above in FIG. 3, the error type is classified as a substitution upon the consensus string of base calls in the look-ahead window matching a string of base calls in the variant read following the position of comparison. As described above in FIG. 4, the error type is classified as a deletion upon the look-ahead window consensus matching the base call at the position of comparison in the variant read and one or more following positions.

As described above in FIG. 5, the error type there is classified as an insertion. It is classified as an insertion because (1) a base call in the variant read following the position of comparison (i.e., the first base call in the look-ahead window for the variant read) matches the plurality consensus base call and (2) the consensus string of base calls in the look-ahead window matching a string of base calls in the variant read equal in length to the look-ahead window and starting two positions following the position of comparison. As described above in FIG. 6, the error type is classified as an indeterminant error if it cannot be classified as a substitution, a deletion, or an insertion.

A trace recovery module 1022 recovers usable portions of a read that has been identified as containing an indeterminant error, rather than discarding the read entirely. The trace recovery module 1022 identifies a position at which a read becomes inactive due to an indeterminant error, omitting or skipping a portion of the read affected by the indeterminant error, and evaluating portions of the read beyond the skipped portion to determine whether the read can be realigned with other reads in the cluster. Upon identifying a candidate position past the indeterminant error at which the read sufficiently matches a consensus derived from active reads, processing of the read may resume for purposes of determining a consensus output sequence.

A consensus output sequence generator 1024 determines a consensus output sequence 204 based at least in part on the plurality consensus bases and the error types identified along the aligned reads. Each position in the consensus output sequence 204 is the plurality consensus base at that position in view of the adjusted alignment of the reads due to error type classification. An error profile of the polynucleotide sequencer 110 and/or quality information of the individual base calls may also be used to determine the consensus output sequence 204 through influencing the identification of plurality consensus bases and error types.

The consensus output sequence generator 1024 may also generate and assemble consensus output sequences for alignments of subsequences defined by alignment anchor sequences. Assembling consensus output sequences for two or more subsequences of a cluster of reads may include generating both a forward consensus sequence and a reverse consensus sequence for each subsequence as shown in FIG. 9. The forward consensus sequence and the reverse consensus output sequences may be combined as described above to create multiple combined consensus sequences for each cluster of reads. The sequence of the alignment anchor(s) is used to append combined consensus sequences together. For example, a first combined consensus sequence representing the first half of a read and a second combined consensus sequence representing a second half of the read may be appended to each other by alignment at the alignment anchor sequence. If multiple alignment anchors are present, multiple combined consensus sequences may be appended in the correct order by alignment at the respective alignment anchor sequences. After appending the two or more combined consensus sequences together, the alignment anchor sequence(s) may be removed to leave a string that is a combined consensus sequence for the reads without the alignment anchor sequences. A combined consensus sequence assembled from multiple subsequences may be more accurate than a combined consensus sequence made from the entire length of a read without alignment anchors because the number of positions traversed (and the number of opportunities for reads to become out of phase with each other) by any forward consensus sequence or reverse consensus sequence is fewer. Reducing the amount of accumulated errors may also reduce the coverage or sequencing depth needed to form clusters that can yield accurate consensus sequences.

An error correction module 1026 may apply additional error correction techniques to decode the consensus output sequence 204. In some implementations, the error correction module 1026 uses a non-binary error-correcting code to decode the consensus output sequence 204 based on redundant data that is encoded into the strands. One example of this type of error correction is Reed-Solomon error correction. In an example implementation, a Reed-Solomon outer code may be added to the starting binary data and ultimately distributed across many strands of DNA (e.g., 10,000-100,000 strands) when stored. It is possible that the Reed-Solomon error correction may fail to decode the consensus output sequence 204 if there are more than a threshold number of errors. If this occurs, trace reconstruction may be repeated with a change in one of the parameters. Changing a parameter may result in a different consensus output sequence 204 that the Reed-Solomon error correction is able to decode. The length of the look-ahead window (w) is one parameter that could be changed. A look-ahead window of length three could be used instead of a look-ahead window of length two (or vice versa). Cut off thresholds for labeling a read as an inactive trace, the length of the delay, accepting a base call based on quality information, and biasing an error type classification for ambiguous errors could all be varied by making them more lenient or stricter. After changing one or more parameters, it can be determined if the consensus output sequence 204 is different from the previous consensus output sequence 204, and if it is, Reed-Solomon error correction may be applied to the new consensus output sequence 204 to see if it is able to decode the sequence.

A conversion module 1028 converts the consensus output sequence into binary data 208 representing at least a portion of a digital file. The conversion from a series of base calls to a string of binary data 208 is performed by reversing the operations that were originally used to encode the binary data 208 as a series of base calls. These operations will be known to the entity that operates the DNA storage library 106. In some implementations, the converter 206 introduced in FIG. 2 may include the same functionalities as the conversion module 1028 as well the error correction module 1026, and possibly other modules. The binary data 208 may be used in the same manner as any other type of binary data. If the various error correction techniques are sufficient, the binary data 208 will represent a perfect reproduction of the original binary data.

Illustrative Processes

For ease of understanding, the processes discussed in this disclosure are delineated as separate operations represented as independent blocks. However, these separately delineated operations should not be construed as necessarily order dependent in their performance. The order in which the process is described is not intended to be construed as a limitation, and any number of the described process blocks may be combined in any order to implement the process or an alternate process. Moreover, it is also possible that one or more of the provided operations is modified or omitted.

Figure 11A:
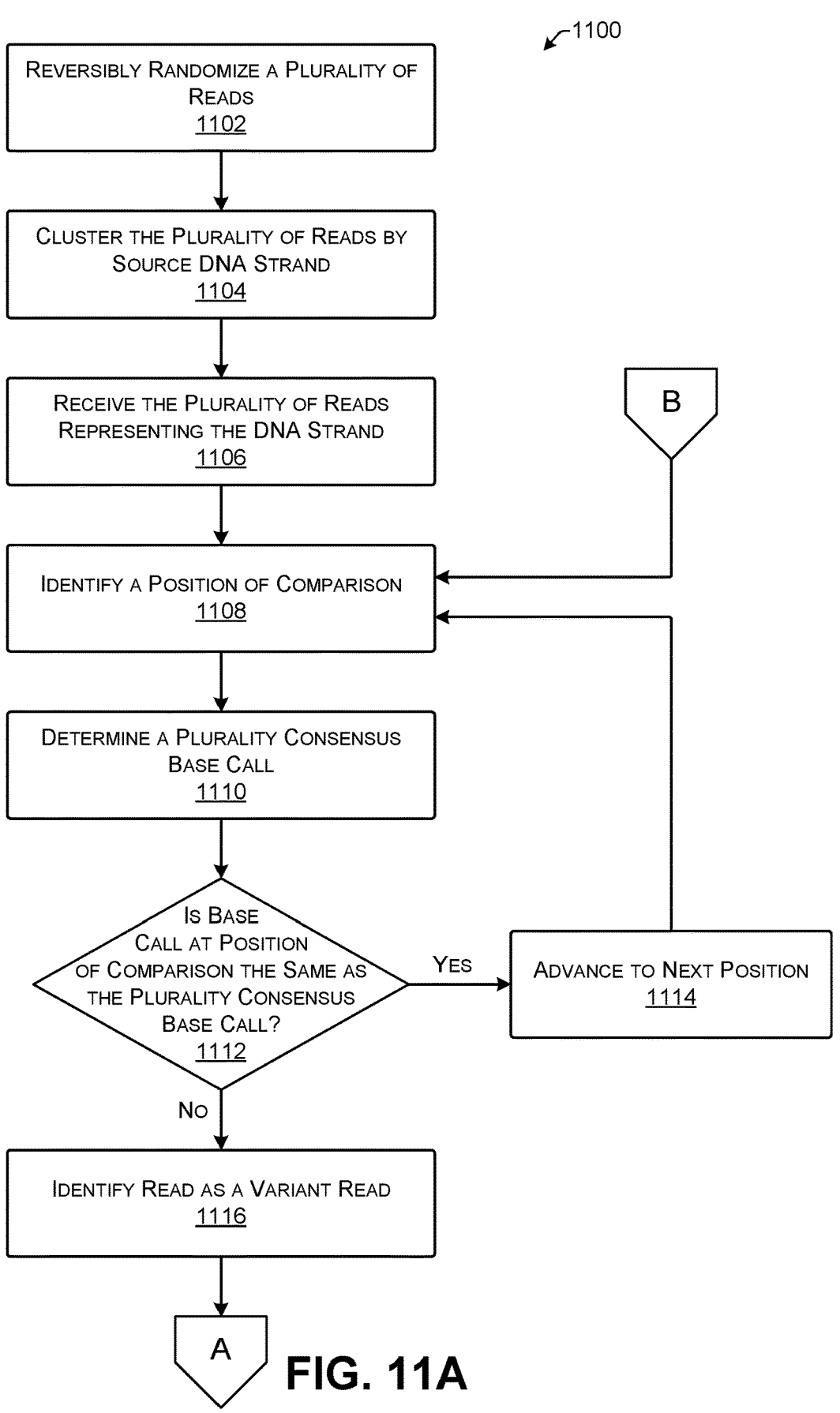
FIGS. 11A and 11B show an illustrative process for determining a consensus output sequence from a plurality of reads.
Figure 11B:
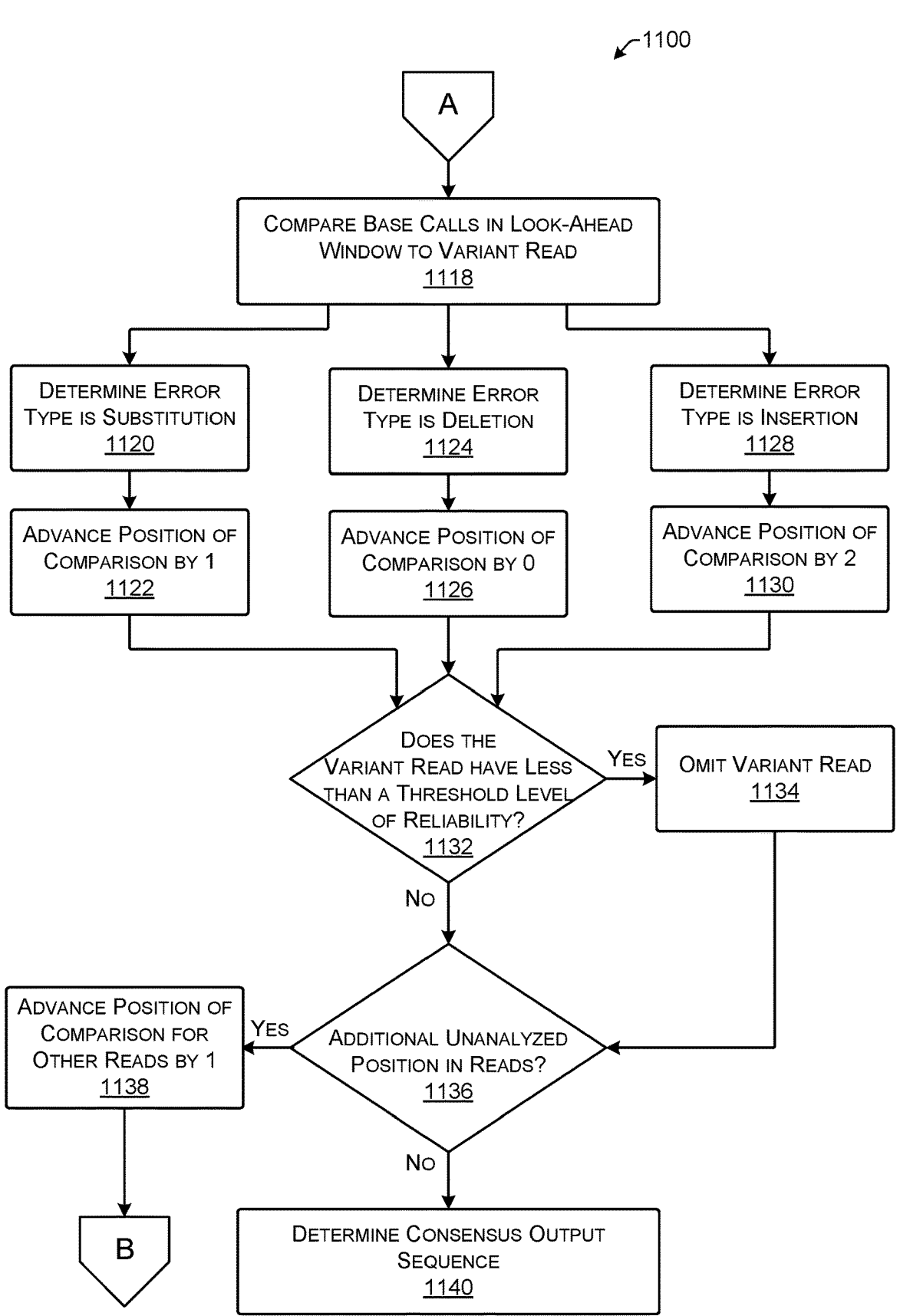

FIGS. 11A and 11B show process 1100 for correcting insertion, deletion, and substitution errors in sequence data generated by a polynucleotide sequencer. The process 1100 may be implemented by the trace reconstruction system 102 shown in FIGS. 1, 2, and 10.

At 1102, binary data to be encoded as one or more DNA strands is reversibly randomized. This randomization occurs before synthesis of DNA strands and in some implementations is present in all reads. The reads may be received via the sequence data interface 1008 shown in FIG. 10. The reads may be randomized by the randomization module 1010 shown in FIG. 10.

At 1104, the sequence data generated by the polynucleotide sequencer are clustered using a clustering technique. Any suitable clustering technique may be used and one of ordinary skill in the art will be able to identify a suitable clustering technique. Clustering creates groups of reads derived from the same source DNA strand. Clustering may be performed by the clusterization module 1012 shown in FIG. 10. In some implementations, performing the clustering on randomized data improves the ability of the clustering technique to separate accurately the plurality of reads into distinct groups. A poorly formed cluster is one that contains reads derived from different DNA strands. Techniques such as discarding reads that deviate more than a threshold amount from a consensus sequence may prevent poorly formed clusters from impacting the final consensus output sequence. However, discarding an entire read loses any useful information that may be obtained from that read.

At 1106, a plurality of reads classified as representing a DNA strand are received for further analysis. The reads may be classified as representing the same DNA strand based on clustering performed at 1104. The plurality of reads may also be classified as representing the same DNA strand due to use of a sequencing technique in which the input for the polynucleotide sequencer is only a single DNA strand (or essentially identical copies thereof produced by PCR). In some implementations, the plurality of reads may be received via the sequence data interface 1008 shown in FIG. 10. In other implementations, the plurality of reads may be received following clustering performed by the clusterization module 1012.

At 1108, a position of comparison spanning the plurality of reads is identified. The position of comparison may be similar to the position of comparison 300 shown in FIG. 3, the position of comparison 400 shown in FIG. 4, the position of comparison 500 shown in FIG. 5, or the position of comparison 600 shown in FIG. 6. In an implementation, the position of comparison may be identified by the read alignment module 1014 shown in FIG. 10.

At 1110, a plurality consensus base call at the position of comparison is determined by identifying the most common base call at that position. Ties may be broken arbitrarily. As described above, the most common base call may be identified in part by consideration of quality information for the base calls present at the position of comparison. In an implementation, the plurality consensus base call may be determined by the variant read identification module 1018 shown in FIG. 10.

At 1112, it is determined if the base call at the position of comparison is the same as the plurality consensus base call. If it is the same, then the read being analyzed has the expected base call at this position, is not a variant read with respect to this position, and process 1100 follows "yes" path to 1114.

At 1114, process 1100 advances to the next position along the read. If, however, the base call at the position of comparison does not match the plurality consensus base call, process 1100 follows "no" path from 1112 to 1116.

At 1116, a read from the plurality of reads that has a base call in the position of comparison that differs from the plurality consensus base call is identified as a variant read. In an implementation, this identification may be performed by the variant read identification module 1018 shown in FIG. 10.

Moving to FIG. 11B, at 1118, a consensus string of base calls in a look-ahead window adjacent to the position of comparison is compared to base calls in the variant read. The consensus string of base calls in the look-ahead window may be limited to the base calls from the subset of reads that has the plurality consensus base call at the position of comparison. For example, in a set of 10 or 20 reads more than one may be variant reads due to the base call at the position of comparison not matching the plurality consensus base call. When a comparison is made for one of the variant reads, the base calls in the look-ahead window of the other variant reads are not considered. This is because the other variant reads may have deletion or insertion errors that would cause the base calls in the look-ahead window to be out of phase and possibly incorrect. A type of error can be determined for the variant read based at least in part on this comparison. In an implementation, this comparison may be performed by the error classification module 1020 shown in FIG. 10. In one implementation, a length of the look-ahead window may be 2-4 positions.

At 1120, the error type for the variant read is determined to be a substitution based on the consensus string of base calls in the look-ahead window being the same as the string of base calls in a look-ahead window following the position of comparison for the variant read. Thus, the look-ahead window of the variant read matches the look-ahead window of the non-variant reads. This relationship is shown, for example, in FIG. 3.

At 1122, the position of comparison for the variant read is advanced one position.

In the alternative, at 1124, the error type for the variant read is determined to be a deletion based on the consensus string of base calls in the look-ahead window being the same as a string of base calls in the variant read including the base call in the position of comparison and adjacent base calls. The length of this string of base calls in the variant read is equal in length to the length of the look-ahead window. Thus, for example, if the length of the look-ahead window is three positions, the string of base calls in the variant read includes the base call in the position of comparison and the next two base calls. This relationship is shown, for example, in FIG. 4.

At 1126, the position of comparison for the variant read is advanced zero positions. Because there is a deletion, not advancing the position of comparison for the variant read re-aligns the strands so that the strands will be in phase for subsequent analysis.

As a further alternative, at 1128, the error type for the variant read is determined to be an insertion based on base calls matching two specific ways. First, a base call in the variant read following the position of comparison is the same as the plurality consensus base call and, second, the consensus string of base calls in the look-ahead window is the same as a string of base calls in the variant read sequence. The string of base calls in the variant read sequence is equal in length to the look-ahead window and a starting position for this string of base calls is two positions after the position of comparison. This relationship is shown, for example, in FIG. 5.

At 1130, the position of comparison for the variant read is advanced by two positions. The position of comparison is advanced one position to account for the insertion and advanced a second position because the position of comparison is advanced one position for all of the non-variant strands. This maintains alignment between the strands for subsequent analysis.

In each of 1120, 1124, and 1128, the error type for the variant read at the position of interest may be determined based at least in part on an error profile associated with the polynucleotide sequencer. Consideration of the error profile of the polynucleotide sequencer may change either or both of the determination of the plurality consensus base call and the consensus string of base calls in the look-ahead window. In an implementation, consideration of the error profile may be performed by the consensus output sequence generator 1024.

At 1132, it is determined if the variant read has less than a threshold level of reliability. The threshold level may be a number of errors in the variant read; a number of errors in the variant that cannot be uniquely classified; a minimum, median, or mode of the confidence levels for base calls in the variant read; or other factor(s). The threshold number may be a number of positions ranging from one to the total number of positions in the variant read. The threshold number may also be a percentage ranging from 1% to 100%. If the variant read has less than the threshold level of reliability, process 1100 proceeds along the "yes" path to 1134.

Figure 13:
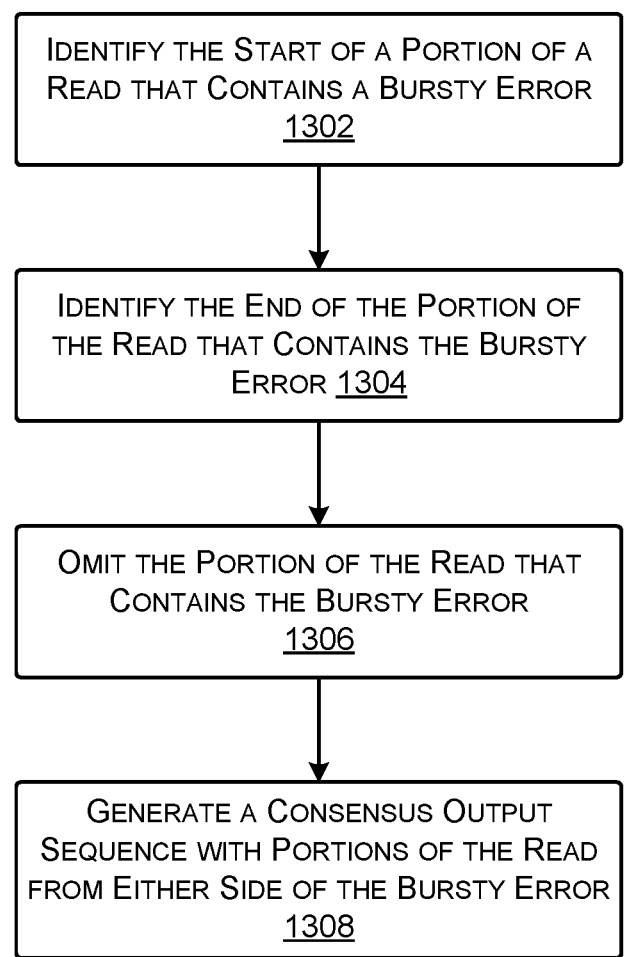
FIG. 13 shows an illustrative process for generating a consensus output sequence by omitting a portion of a read that contains a bursty error.

At 1134, the variant read is omitted and a single consensus output sequence from the plurality of reads is determined without using the variant read. Following omission of the variant read, process 1100 proceeds to 1136. Alternatively, if the variant read does not have less than the threshold level of reliability (i.e., it is considered reliable) the variant read is used for further analysis and process 1100 proceeds along the "no" path to 1136. If the variant read is classified as such due to the presence of an indeterminate error that cannot be classified as an insertion, deletion, or substitution, instead of discarding the read, it may be analyzed further as shown in FIG. 13 and/or FIG. 14 below.

At 1136, it is determined if there are additional unanalyzed positions in the reads. Thus, it is determined if the "end" of the reads has been reached and a plurality consensus base call has been identified for the positions of the reads. The end of the reads may also be identified by an alignment anchor if used to break the read into multiple smaller segments. If the analysis has not yet reached the end, then process 1100 proceeds along the "yes" path to 1138.

At 1138, the position of the subset of the plurality of reads having the plurality consensus base call at the position of comparison (i.e., the non-variant reads) is advanced by one. The new position of comparison for the variant read is advanced by an amount based on the identified error type at 1122, 1126, or 1130. The new position of comparison may be similar to new positions of comparison 312, 412, 512, and 608, shown in FIGS. 3-6. Process 1100 then returns to 1108 and analysis continues.

At 1136, if there are no unanalyzed positions in the reads, then process 1100 proceeds along the "no" path to 1140.

At 1140, a single consensus output sequence is determined based in part on the plurality consensus base call and the error type. The single consensus output sequence may be determined by the consensus output sequence generator 1024 shown in FIG. 10.

Figure 12A:
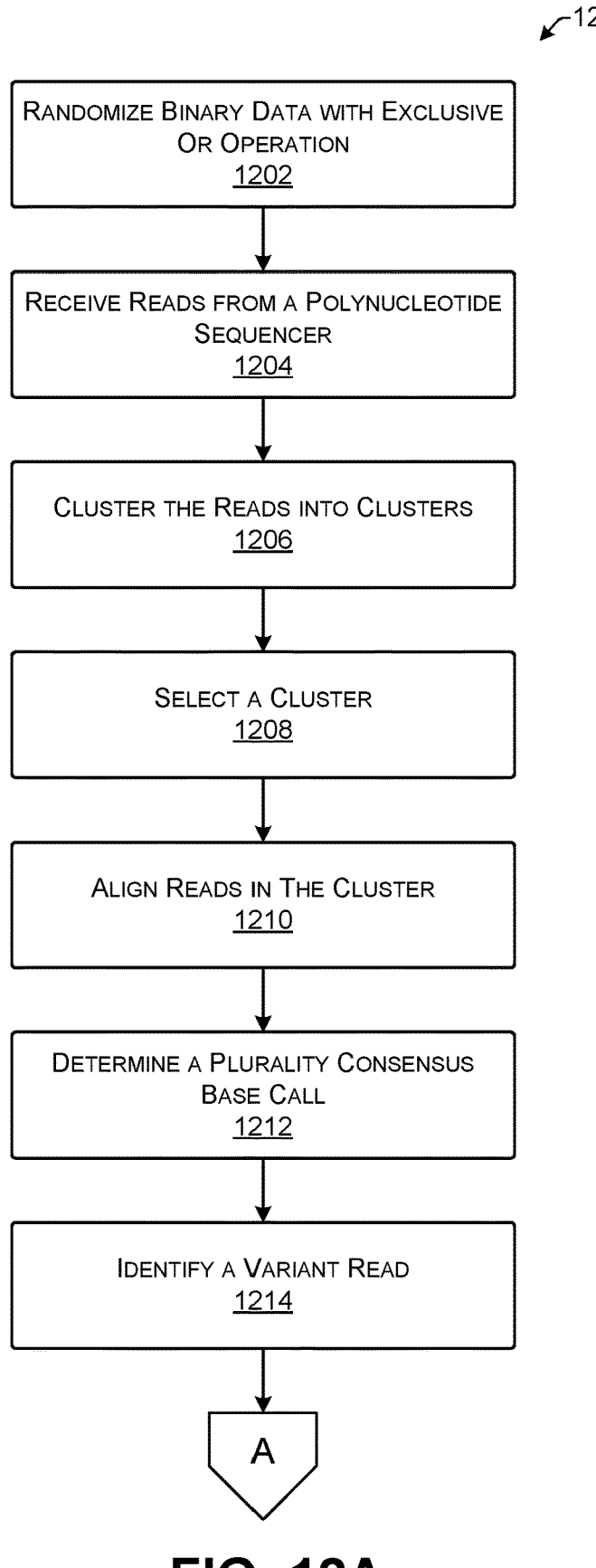

FIGS. 12A and 12B show process 1200 for recovering binary data encoded in a synthetic DNA strand by accounting for insertion, deletion, and/or substitution errors. The process 1200 may be implemented by the trace reconstruction system 102 shown in FIGS. 1, 2, and 10.

At 1202, binary data to be encoded as DNA is reversibly randomized by taking the exclusive or (XOR) of the binary data and a random sequence generated by a seed and a function. This operation affects the DNA strands that, when read, produce reads that also have characteristics of being randomized. In an implementation, the randomization may be performed by the randomization module 1010 shown in FIG. 10.

At 1204, a plurality of reads are received from a polynucleotide sequencer. In an implementation, the plurality of reads may be received by the sequence data interface 1008 shown in FIG. 10.

At 1206, the plurality of reads is clustered into a plurality of clusters by sequence similarity. Similar sequences are likely to have originated from sequencing of the same DNA strand (the sequences are not identical due to errors introduced by the polynucleotide sequencer). Thus, one cluster should represent all the reads that came from the same DNA strand. Recall that the polynucleotide sequencer may sequence multiple different DNA strands simultaneously so the raw output of sequence data from the polynucleotide sequencer could include reads that correspond to the multiple different DNA strands. In an implementation, clustering may be performed by the clusterization module 1012 shown in FIG. 10.

At 1208, a cluster is selected from the plurality of clusters. The cluster contains a clustered set of reads. If the clustering was accurate, all the reads in the clustered set of reads come from sequencing of the same DNA strand. At this point, prior to additional analysis, the cluster is identified only by its characteristic of having reads that cluster together. So, in some implementations, each cluster is analyzed in turn and the order of selecting individual clusters may be arbitrary. Multiple ones of the clusters may also be analyzed in parallel. In an implementation, selection of a cluster may be performed by the clusterization module 1012 shown in FIG. 10. Analysis may continue until trace reconstruction is performed on all clusters from the plurality of clusters.

At 1210, the clustered set of reads are aligned at a position of comparison spanning the clustered set of reads. In an implementation, the position of comparison may be the first position shared across the clustered set of reads. Thus, this original alignment may define a first position of comparison. The first position may be the left-most position (corresponding to the 5' end) or alternatively the right-most position (corresponding to the 3' end). In an implementation, alignment may be performed by the read alignment module 1014 shown in FIG. 10.

At 1212, a plurality consensus base call at the first position of comparison is determined. The plurality consensus base call is based at least in part on a most common base call across the clustered set of reads. The plurality consensus base call may be based in further part on an error profile associated with the polynucleotide sequencer. That is to say, base calls may be weighted based on the associated error profile (e.g., more certain base calls count for more and less certain base calls have less influence on the determination of the plurality consensus base call).

At 1214, a variant read from the clustered set of reads is identified. The variant read has a base call at the position of comparison that is different from the plurality consensus base call. In an implementation, the variant read may be identified by the variant read identification module 1018 shown in FIG. 10.

Moving now to FIG. 12B, at 1216, a consensus string of base calls in a look-ahead window is identified. The consensus string is based on base calls for a subset of the clustered set of reads having the plurality consensus base call at the position of comparison (i.e., not variant reads). The look-ahead window is adjacent to the position of comparison. In some implementations, the look-ahead window may be two or three positions long.

At 1218, it is determined that an error type for the variant read at the position of comparison is a substitution based at least in part on base calls in a look-ahead window of the variant read matching the consensus string of base calls. An example of this relationship is shown in FIG. 3. In an implementation, the error type may be determined by the error classification module 1020.

At 1220, the position of comparison for the variant strand is moved ahead by one position.

At 1222, it is determined that an error type for the variant read at the position of comparison is a deletion based at least in part on a series of base calls in the variant read including the base call at the position of comparison and one or more base calls following the position of comparison matching the consensus string of base calls. An example of this relationship is shown in FIG. 4. In an implementation, the error type may be determined by the error classification module 1020.

At 1224, the position of comparison for the variant strand is moved ahead by zero positions.

At 1226, it is determined that an error type for the variant read at the position of comparison is an insertion. An insertion error is identified based at least in part on a base call in the variant read following the position of comparison matching the plurality consensus base call and a series of base calls in the variant read starting two positions following the position of comparison matching the consensus string of base calls. An example of this relationship is shown in FIG. 5. In an implementation, the error type may be determined by the error classification module 1020.

At 1228, the position of comparison for the variant strand is moved ahead by two positions.

At 1230, the position of comparison for reads in the subset of the clustered set of reads (i.e., the non-variant reads) is advanced ahead one position.

At 1232, a single consensus output sequence is determined from the clustered set of reads. In an implementation, the single consensus output sequence generated by the consensus output sequence generator 1024 shown in FIG. 10.

At 1234, the single consensus output sequence in converted into binary data. This may be the final manipulation of the information derived from the DNA strand before it is again used as a digital computer file. In an implementation, the change from sequence data to binary data may be performed by the conversion module 1028 shown in FIG. 10.

FIG. 13 shows process 1300 for identifying a portion of a read that contains a bursty error and generating a consensus output sequence with parts of that read other than the portion that contains the bursty error. Process 1300 may be performed together with either processes 1100 or 1200 as an alternative to discarding the entire read. As described above, the read may be generated from a DNA strand that stores digital data.

At 1302, the start of a portion of the read that contains the bursty error is identified. The start of the portion of the read that contains the bursty error may be identified by detection of the error itself. For example, in a read that does not match a consensus sequence (a variant read) a position that is not classified as an insertion, deletion, or a substitution may be interpreted as the start of the portion of the read that contains the bursty error. An example of identifying an indeterminate error is shown in FIG. 6.

At 1304, an end of the location that contains the bursty error is identified.

Identifying the end of the location that contains the bursty error finds a position in the read that is past the location of the bursty error so that further analysis farther down the read will find a sequence that can align with other reads in the cluster. The end of the bursty error is identified by a candidate position in the read. The candidate position is flanked by one or both of a match-backwards region (mb) or a match-forward region (mf). As described above, the match-backwards region matches a consensus sequence generated from other ones of the plurality of reads in the same cluster and the match-forward sequence matches a sequence generated by plurality voting from the sequences of other reads in the cluster.

At 1306, the portion of the read that contains the bursty error is omitted from generation of the consensus output sequence. Thus, the corresponding positions of the read between the position that is identified as the start of the bursty error and that position is identified as the end of the bursty error do not contribute to determining the consensus output sequence. For these positions in the consensus output sequence the base calls are determined based on some or all of the other reads in the cluster using techniques such as those illustrated in FIG. 11 and FIG. 12.

At 1308, the consensus output sequence is generated with portions of the read on either side of the portion that contains the bursty error. Thus, even though part of the read is not used to generate the consensus output sequence, other portions of the read are used. The portions of the read on either side of the portion with the bursty error are used to generate the consensus output sequence with the techniques described above by comparing values with the plurality of reads at a position of comparison while aligning the plurality of reads with respect to each other based on insertions, deletions, and substitutions. The consensus output sequence may be generated by the consensus output sequence generator 1024.

Figure 14:
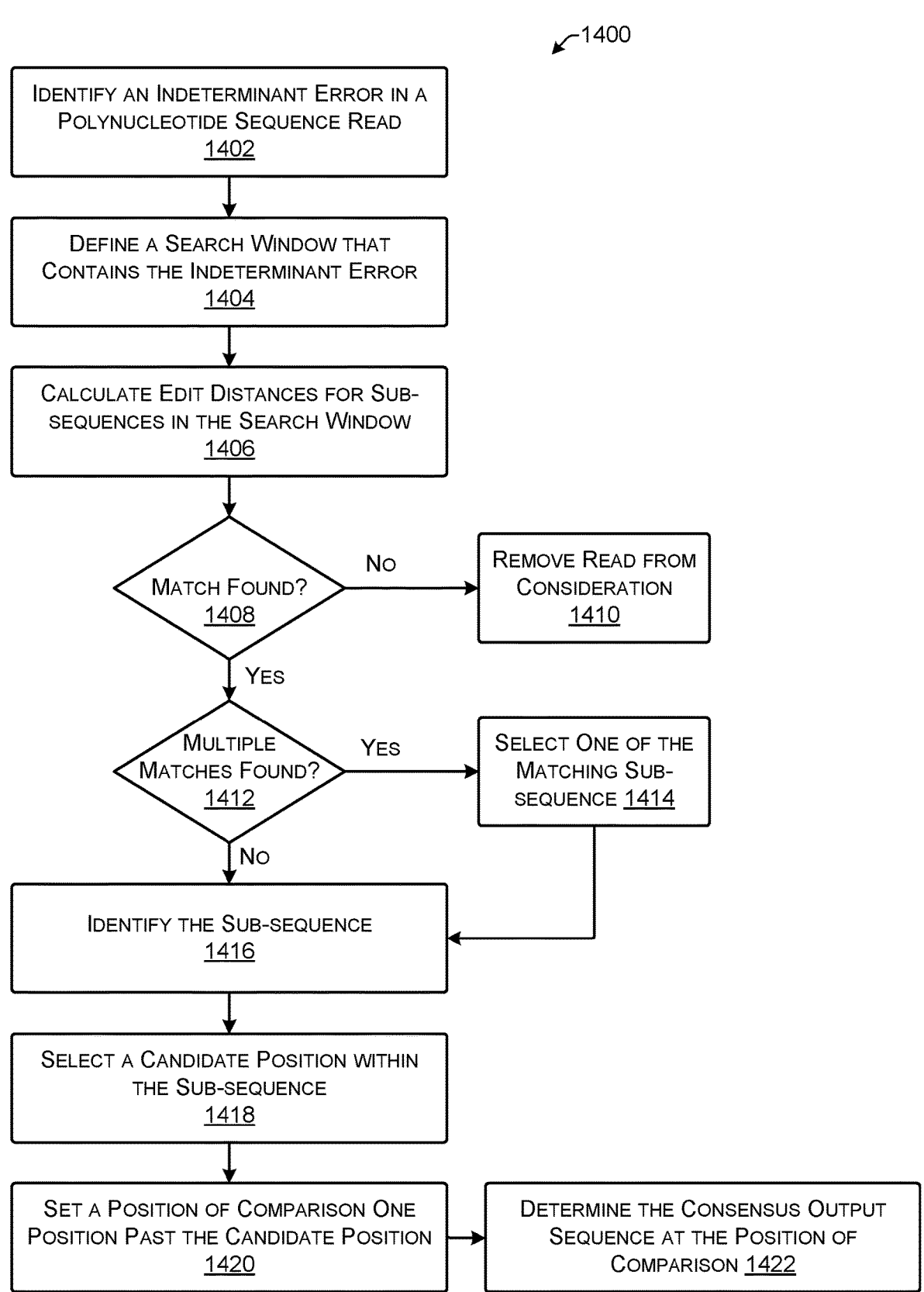
FIG. 14 shows an illustrative process for analyzing a read containing an indeterminant error in determining if there is a subsequence past the location of the indeterminant error that matches with other reads.

FIG. 14 shows process 1400 for determining if a read with an indeterminate error can be "brought back" by finding a matching sequence further down the read. Process 1400 may be performed together with either processes 1100 or 1200 as an alternative to discarding the entire read if the read includes an indeterminate error. The indeterminate error may be a bursty error that is not classified as any of an insertion, a deletion, or a substitution.

At 1402, an indeterminate error is identified in a read which is one of a plurality of reads of polynucleotide sequencer. The plurality of reads may be a group of reads in the same cluster as formed by, for example, the clusterization module 1012. The indeterminate error is an error relative to a consensus output sequence of the plurality of reads. The consensus output sequence may be generated by the consensus output sequence generator 1024.

The indeterminate error may be identified as shown in FIG. 6. Additionally, identification of the error as an indeterminate error may be performed by the error classification module 1020. The indeterminate error is located at a first position in the read. For example, the indeterminate error may be located at position 100 in a read with a total length of 200 base pairs. Thus, the consensus output sequence may be identified for positions 1-99 prior to determining that there is an indeterminate error at position 100.

At 1404, a search window is defined that includes a second position in the read located at a distance at least delay past the first position. In an implementation, the second position is the position represented by $k_0$. In an implementation, a length of the delay may be between 4 and 10 positions. For example, if the delay distance is 8 positions then the search window is a window that includes position

108 in this example read. The search window possibly contains some positions that have base calls which are not in error.

Limiting the search to a search window rather than the entire remainder of that read focuses the search for a matching sequence to an area near where a matching sequence, if it exists, should be found. A shorter search window makes it less likely that a matching sequence will be identified, but a longer search window increases the probability of a false positive match. In an implementation, a length of the search window may be between 9 and 20 positions. As described above, the search window may include two portions: a backward search window (bsw) for positions before $k_0$ and a forward search window (fsw) for positions after $k_0$. The bsw and fsw may be the same length as each other. For example, both the bsw and the fsw may be about 5-8 positions long. Thus, the search window includes the bsw, $k_0$, and the fsw.

At 1406, edit distances are calculated for subsequences in the search window as determined from a comparison sequence. The comparison sequence may include a match-backward sequence (mb) that is that consensus output sequence of corresponding positions in some or all of the other reads in the plurality of sequence reads. The length of the match-backwards sequence may be about 1-11 positions.

The consensus output sequence of the plurality of sequence reads may be determined by identifying a plurality vote for the position of consideration while accounting for insertion errors, deletion errors, and substitution errors, and proceeds sequentially from a base call position currently under consideration to an adjacent base call position. Thus, all of the other reads from the same cluster (or all of the other reads that do not also have indeterminate errors at this position) may be used to generate a consensus output sequence as described above.

The comparison sequence may also include a match-forward sequence (mf). As described above, the match-forward sequence is adjacent to the match-backward sequence and positioned past the location of the match-backward sequence (i.e., further away from the location of the indeterminate error). The match-forward sequence corresponds to a portion of the aligned reads for which the consensus output sequence has not yet been determined. Because the consensus output sequence has not been determined for the positions included in the match-forward sequence, a plurality consensus vote from the base calls of the other reads in the cluster is used to determine if there is a match. The plurality consensus vote simply identifies the most frequent base call at each position without attempting to account for errors such as insertions, deletions, and substitutions. If the match-forward sequence is included, a length of the match-forward sequence is 1-10 positions.

In an implementation, a sliding window may be moved across the search window and the sequence within the sliding window may be used as the subsequence which is compared to the consensus output sequence. Edit distance can be calculated for each of the positions of the sliding window. Depending on its position, the sliding window may include relatively more or relatively less of the match-backward sequence and the match-forward sequence.

At 1408, it is determined if a match is found between any of the subsequences and the consensus output sequence at the corresponding positions. A match is identified by the edit distance being equal to or less than a threshold value. For example, if the threshold value is 0, then only exact matches with an edit distance equal to the threshold value of 0 are treated as matching. If the threshold value for the edit distance is 1, then two sequences that have a single base call difference can be classified as matches as well as sequences that have an edit distance of less than the threshold value (i.e., exact matches with an edit distance of 0).

If no match is found, then process 1400 proceeds along "no" path to 1410 and the read is removed from consideration. The lack of a match indicates that there is no subsequence within the search window that matches with the consensus output sequence/plurality consensus vote. Thus, the read may have extensive errors and the most accurate consensus output sequence may be obtained by ignoring this read.

If, however, a match is found, then process 1400 proceeds along the "yes" path to 1412. At 1412, it is determined if multiple matches are found. Within the search window there may be more than one subsequence that matches the corresponding base calls of the consensus output sequence. If this is the case, then process 1400 proceeds along "yes" path to 1414.

At 1414, one of the matching subsequences is selected. Out of two or more matching subsequences, one may be selected by any of a number of techniques such as random selection, selecting the one of the subsequences that is closest to the beginning of the read (e.g., 5'-end), selecting the one of the subsequences that is farthest from the beginning of the read, or by another criteria.

At 1416, a single subsequence in the search window with an edit distance less than a threshold value is identified. This is a matching subsequence indicating that following the location of the indeterminate error, there is a portion of the read that once again can be aligned with the other reads in the cluster.

At 1418, a candidate position within the matching subsequence is selected. The matching subsequence may have a length of about 5-15 positions and one of those positions is selected for use as the candidate position. The candidate position may be the same as the candidate position (k) shown in FIG. 7. In an implementation, the candidate position may be the position in the match-backward sequence that is farthest from the position where the indeterminate error begins. Thus, if there is no match-forward sequence, then the candidate position may be the position within the matching subsequence at the end of the matching subsequence. If there is a match-forward sequence, then the candidate position may be the position in the match-backward sequence directly adjacent to the match-forward sequence.

At 1420, a position of comparison is set one position past the candidate position. The position of comparison may be the same as the position of comparison 600 shown in FIG. 6. Thus, the location of the matching subsequence and the candidate position are used to determine how to realign this read with the other reads following the indeterminate error. The position of comparison is located at a third position in the read which, using the notation introduced above, may be indicated as being located at k+1.

At 1422, the consensus output sequence from the plurality reads is determined at the third position. This position of comparison is used to compare the read as well as other reads in the cluster to determine a consensus output sequence as described above. Analysis of the read may continue until the end of the read is reached and any variations in the read from the output sequence may be handled as described earlier in this disclosure.

Many of the parameters used to identify a matching subsequence and ultimately determine the position of comparison such as the delay, bsw, fsw, mb, and mf have lengths that can vary. The lengths used to analyze a given set of sequence data may be determined experimentally by testing different values for the length of each of the delay, search window, mb, and mf. Each may be varied within a range of values and different combinations may be tested.

For each combination of lengths, a number of clusters that can be generated from the reads produced by the polynucleotide sequencer is determined. Generating a larger number of clusters indicates that more of the reads are able to be used even with indeterminate errors and that more of the data output by the polynucleotide sequencer is contributing to generation of consensus output sequences. Thus, the combination of values that results in formation of a largest number of clusters of reads from the plurality of sequence reads may be used as the lengths for the parameters.

EXAMPLES

The techniques described in this disclosure were tested on three different files generated by Nanopore sequencing with sizes 32 kB, 115 kB, and 1500 kB. Each of these files contained digital information that was encoded in the sequence of the DNA strands. This was not synthetic data, but actual computer files encoded in DNA. Thus, the qualitative test of this technique was in part a test of the ability to successfully recover the files from DNA strands. The quantitative metrics are the number of clusters correctly recovered from the output of the polynucleotide synthesizer and coverage depth of the sequencing.

This novel technique that ignores portions of reads which contain indeterminate errors while using portions that do not ("new technique") was compared to an earlier technique which attempts to classify an error as either an insertion, deletion, or a substitution and discards the entire read from further consideration if the error cannot be classified as one of these three types ("old technique"). For each of the two smaller files, the new technique produced better results as measured by cluster recovery and coverage.

The number of clusters correctly recovered is indicative of the number of unique DNA strands for which the analysis can generate a consensus sequence. The total number of clusters is the number of clusters formed including clusters that do not yield a consensus sequence. Thus, recovering a larger number of clusters indicates recovery of the sequences from a greater number of DNA strands. The comparisons are presented in Table 1 below.

TABLE 1

Comparison of cluster recovery between two different techniques for trace reconstruction from multiple noisy reads.

| File Size (kilobytes) | Clusters Total No. | Clusters Recovered Correctly | | Improvement (%) |
| | | Old Technique | New Technique | |
|---|---|---|---|---|
| 32 | 4021 | 1637 | 1675 | 2.32 |
| 115 | 10950 | 5723 | 5910 | 3.27 |

Thus, the new technique recovered between 2-4% more clusters correctly. The largest file of 1500 kB was not able to be decoded using the old technique (thus, no comparative cluster recovery values) but was successfully decoded using the new technique. Approximately 5000 different parameter combinations were tested by trying various values for delay, search window forwards (swf), search window backwards (swb), match backwards (mb), and match-forwards (mf) to see what combination would generate the largest number of correct clusters. For all of the test results shown in Table 1, the distance threshold (dt) was set to zero, thus requiring exact matches. The swf and swb were set to the same value as indicated in the sw(f/b) column. The parameters that produced the largest number of correct clusters for the 32 kB file and the 115 kB file are shown in Table 2 below. Four different combinations of parameters that were successful for decoding the 1500 kB file are also shown in Table 2.

TABLE 2

Comparison of parameter values used for the new technique to successfully decode files and maximize the number of clusters correctly recovered.

| File Size (kilobytes) | Delay | Sw(f/b) | mb | mf |
|---|---|---|---|---|
| 32 | 8 | 8 | 7 | 0 |
| 115 | 6 | 5 | 1 | 8 |
| 1500 | 5 | 5 | 5 | 5 |
| 1500 | 8 | 8 | 5 | 5 |
| 1500 | 8 | 8 | 8 | 0 |
| 1500 | 8 | 8 | 0 | 8 |

For the files tested, the delay length was 5-8 and the search window (forwards and backwards) was also 5-8. Either the match-forward or the match backward region could be omitted as indicated by the examples in which the length is 0. However, for all the examples shown in Table 2 the combined length of the match backward and match-forward regions was 7-10.

Furthermore, the new technique was able to recover the files with lower coverage levels. For the 32 kB file, it was successfully decoded with 22× coverage using the new technique but the old technique failed to decode it at 38× coverage. The 115 kB file decoded successfully at 27× coverage but using the old technique 32× coverage was insufficient. For the large, 1500 kB, file it was successfully decoded with 27.2× coverage. Testing with random subsamples of the 1500 kB file determined that it could be recovered with coverage as low as 23.1×. All of the tested samples could be recovered with 27× coverage or less using this new technique, while the old technique when it could successfully recover a file needed a depth of coverage well over 30×. Reduced coverage allows for decoding of the digital information stored in DNA with less sequencing and less expense as compared to a higher level of coverage.

ILLUSTRATIVE EMBODIMENTS

The following clauses describe multiple possible embodiments for implementing the features described in this disclosure. The various embodiments described herein are not limiting nor is every feature from any given embodiment required to be present in another embodiment. Any two or more of the embodiments may be combined together unless context clearly indicates otherwise. As used herein in this document "or" means and/or. For example, "A or B" means A without B, B without A, or A and B. As used herein, "comprising" means including all listed features and potentially including addition of other features that are not listed. "Consisting essentially of" means including the listed features and those additional features that do not materially affect the basic and novel characteristics of the listed features. "Consisting of" means only the listed features to the exclusion of any feature not listed.

Clause 1. A method of generating a consensus sequence from a plurality of reads of a deoxyribose nucleic acid (DNA) strand that stores digital data, the plurality of reads generated with less than 30× coverage by a sequencing technology that introduces a bursty error into a read of the plurality of reads, the method comprising: omitting a portion of the read that contains the bursty error from generation of a consensus output sequence; and generating the consensus output sequence with portions of the read from either side of the portion of the read that contains the bursty error.

Clause 2. The method of clause 1, wherein the sequencing technology is Nanopore sequencing.

Clause 3. The method of any of clauses 1-2, wherein the plurality of reads are generated with less than 25× coverage.

Clause 4. The method of any of clauses 1-3, further comprising identifying a start of the portion of the read that contains the bursty error by identifying a position in the read that does not match the consensus sequence and is not classified as an insertion, a deletion, or a substitution.

Clause 5. The method of any of clauses 1-4, further comprising identifying an end of the portion of the read that contains the bursty error by identifying a position in the read that is flanked by at least one of a match-backwards region that matches the consensus sequence or a match-forwards region that matches a sequence generated by plurality voting from sequences of at least two other reads of the plurality of reads.

Clause 6. The method of any of clauses 1-5, wherein the consensus sequence is generated by comparing values for the plurality of reads at a position of comparison while aligning the plurality of reads with respect to each other based on insertions, deletions, and substitutions.

Clause 7. Computer-readable media encoding instructions which when executed by a processing unit cause a computing device to perform the method of any of clauses 1-6.

Clause 8. A system comprising a processing using and memory configured to implement the method of any of clauses 1-6.

Clause 9. A method comprising: identifying, in a read of a plurality of sequence reads from a polynucleotide sequencer, an indeterminant error relative to a consensus output sequence of the plurality of sequence reads, the indeterminant error located at a first position; defining a search window that includes a second position in the read, the second position located at a distance at least delay past the first position; calculating edit distances for subsequences in the search window from a comparison sequence, the comparison sequence including a match-backwards sequence that is a consensus output sequence of corresponding positions in at least two of the plurality of sequence reads; identifying a subsequence in the search window that has an edit distance less than a threshold value; selecting a candidate position within the subsequence based on a length of the match-backwards sequence; setting a position of comparison to at least two other reads from the plurality of sequence reads to a third position in the read that is one position past the candidate position; and determining the consensus output sequence from the plurality of sequence reads at the third position.

Clause 10. The method of any of clause 9, wherein the indeterminant error is a bursty error that is not classified as any of an insertion, a deletion, or a substitution.

Clause 11. The method of any of clauses 9-10, wherein the consensus output sequence of the plurality of sequence reads is determined by identifying a plurality vote for a position of consideration while accounting for insertion errors, deletion errors, and substitution errors and proceeds sequentially from a base call position currently under consideration to an adjacent base call position.

Clause 12. The method of any of clauses 9-11, further comprising identifying a second subsequence in the search window that has an edit distance less than the threshold value and selecting the one of the subsequence or the second subsequence that is closest to the candidate position.

Clause 13. The method of any of clauses 9-12, wherein the threshold value for the edit distance is 0.

Clause 14. The method of any of clauses 9-13, wherein the comparison sequence also includes a match-forward sequence that is a plurality consensus vote for base calls from at least the two other reads from the plurality of sequence reads.

Clause 15. The method of clause 14, wherein a length of the delay is between 4 and 10 positions, a length of the search window is between 9 and 20 positions, a length of the match-backwards sequence is between 1 and 11 positions, and a length of the match-forward sequence is between 1 and 10 positions.

Clause 16. The method of clause 15, wherein a sum of the length of the match-backwards sequence and the length of the match-forward sequence is between 5 and 15 positions.

Clause 17. The method of clause 15 or 16, wherein a length of the delay, a length of the search window, a length of the match-backwards sequence, and a length of the match-forward sequence are each determined experimentally by testing different values for each length and selecting a combination of values that results in recovery of a largest number of clusters of reads from the plurality of sequence reads.

Clause 18. Computer-readable media encoding instructions which when executed by a processing unit cause a computing device to perform the method of any of clauses 9-17.

Clause 19. A system comprising a processing using and memory configured to implement the method of any of clauses 9-17.

Clause 20. A system for aligning of sequence reads comprising: one or more processing units; a memory coupled to the one or more processing units; an alignment anchor module stored in the memory and implemented by the one or more processing units to: identify an alignment anchor sequence having a predetermined sequence that is present in a first sequence read and in a second sequence read, divide the first sequence read into a first sub-read that extends from a beginning of the first sequence read to the alignment anchor sequence and into a second sub-read that extends from the alignment anchor sequence to an end of the first sequence read, divide the second sequence read into a third sub-read that extends from the beginning of the second sequence read to the alignment anchor sequence and into a fourth sub-read that extends from the alignment anchor sequence to the end of the second sequence read; and a read alignment module stored in the memory and implemented on the one or more processing units to: align the first sub-read with the third sub-read based on the beginning of the first sequence read, the beginning of the second sequence read, and the alignment anchor sequence, and align the second sub-read with the fourth sub-read based on the alignment anchor sequence, the end of the first sequence read and the end of the second sequence read.

Clause 21. The system of clause 20, wherein the alignment anchor sequence has a sequence that does not align with itself.

Clause 22. The system of any of clauses 20-21, wherein the alignment anchor sequence is located between 45% and 55% of distance from the beginning of the first sequence read to the end of the first sequence read and located between 45% and 55% of distance from the beginning of the second sequence read to the end of the second sequence read.

Clause 23. The system of any of clauses 20-22, further comprising an oligonucleotide synthesizer configured to synthesize a first polynucleotide molecule with the first sequence read that includes only one instance of the alignment anchor sequence and to synthesize a second polynucleotide sequence with the second polynucleotide sequence that includes only one instance of the alignment anchor sequence.

Clause 24. The system of any of clauses 20-23, further comprising a consensus output sequence generator module stored in the memory and implemented on the one or more processing units to: generate a first forward consensus sequence from the first sub-read and the third sub-read; generate a first reverse consensus sequence from the first sub-read and the third sub-read; combine the first forward consensus sequence and the first reverse consensus sequence into a first combined consensus sequence; generate a second forward consensus sequence from the second sub-read and the fourth sub-read; generate a second reverse consensus sequence from the second sub-read and the fourth sub-read; combine the second forward consensus sequence and the second reverse consensus sequence into a second combined consensus sequence; append the second combined consensus sequence to an end of the first combined consensus sequence by alignment at the alignment anchor sequence; and remove the alignment anchor sequence.

Clause 25. A system for aligning of sequence reads comprising: one or more means for processing; a memory coupled to the one or more means for processing; means for identifying an alignment anchor sequence having a predetermined sequence that is present in a first sequence read and in a second sequence read, means for dividing the first sequence read into a first sub-read that extends from a beginning of the first sequence read to the alignment anchor sequence and into a second sub-read that extends from the alignment anchor sequence to an end of the first polynucleotide sequence, means for dividing the second sequence read into a third sub-read that extends from the beginning of the second sequence read to the alignment anchor sequence and into a fourth sub-read that extends from the alignment anchor sequence to the end of the second polynucleotide sequence; means for aligning the first sub-read with the third sub-read based on the beginning of the first sequence read, the beginning of the second sequence read, and the alignment anchor sequence, and means for aligning the second sub-read with the fourth sub-read based on the alignment anchor sequence, the end of the first sequence read and the end of the second sequence read.

CONCLUSION

Although the subject matter has been described in language specific to structural features and/or methodological acts, it is to be understood that the subject matter defined in the appended claims is not necessarily limited to the specific features or acts described above. Rather, the specific features and acts are disclosed as example forms of implementing the claims.

All publications referenced herein are incorporated by reference both for the specific teachings for which the individual publications are cited and for everything disclosed within the referenced publications.

---

The invention claimed is:

1. A method of recovering stored digital data comprising:

sequencing a deoxyribose nucleic acid (DNA) strand with a sequencing technology, wherein the DNA strand stores digital data thereby generating a plurality of reads;

generating a consensus output sequence from the plurality of reads of the DNA strand, the plurality of reads generated with less than 30× coverage by the sequencing technology that introduces a bursty error that includes multiple adjacent errors into a read of the plurality of reads by:

identifying a start of a portion of the read that contains the bursty error by identifying a position in the read that does not match a consensus sequence and cannot be classified as an insertion, a deletion, or a substitution after attempting such classification;

identifying an end of the portion of the read that contains the bursty error by identifying a position in the read that is flanked by a match-backwards region that matches a consensus sequence generated from the plurality of reads;

omitting only the portion of the read that contains the bursty error from generation of the consensus output sequence;

generating the consensus output sequence with portions of the read from either side of the portion of the read that contains the bursty error; and converting the consensus output sequence into the digital data.

2. The method of claim 1, wherein the sequencing technology is Nanopore sequencing.

3. The method of claim 1, wherein the plurality of reads are generated with less than 25× coverage.

4. The method of claim 1, wherein the consensus output sequence is generated by comparing values for the plurality of reads at a position of comparison while aligning the plurality of reads with respect to each other based on insertions, deletions, and substitutions.

5. The method of claim 4, wherein comparing values for the plurality of reads comprises determining a plurality consensus base.

6. The method of claim 1, further comprising identifying an end of the portion of the read that contains the bursty error by identifying a position in the read that is flanked by a match-forwards region that matches a sequence generated by plurality voting from sequences of at least two other reads of the plurality of reads.

7. A system for recovering stored digital data comprising:

a polynucleotide sequencer implementing a sequencing technology and configured to sequence a deoxyribose nucleic acid (DNA) strand to generate a plurality of reads, wherein the DNA strand stores digital data;

one or more processing units;

a memory coupled to the one or more processing units;

a sequence data interface configured to receive the plurality of reads of the DNA strand that were generated with less than 30× coverage by the sequencing technology that introduces a bursty error that includes multiple adjacent errors into a read of the plurality of reads;

a consensus output sequence generator stored in the memory and implemented by the one or more processing units to:

identify a start of a portion of the read that contains the bursty error by identifying a position in the read that does not match a consensus sequence and cannot be classified as an insertion, a deletion, or a substitution after attempting such classification;

identify an end of the portion of the read that contains the bursty error by identifying a position in the read that is flanked by a match-backwards region that matches a consensus sequence;

omit only the portion of the read that contains the bursty error from generation of a consensus output sequence; and generate the consensus output sequence with portions of the read from either side of the portion of the read that contains the bursty error; and a conversion module configured to convert the consensus output sequence into digital data.

8. The system of claim 7, wherein the sequencing technology of the polynucleotide sequencer is Nanopore sequencing.

9. The system of claim 7, wherein the plurality of reads are generated with less than 25× coverage.

10. The system of claim 7, wherein the consensus output sequence generator is further configured to generate the consensus output sequence by comparing values for the plurality of reads at a position of comparison while aligning the plurality of reads with respect to each other based on insertions, deletions, and substitutions.

11. The system of claim 10, wherein comparing values for the plurality of reads comprises determining a plurality consensus base.

12. The system of claim 7, wherein the consensus output sequence generator is further configured to identify an end of the portion of the read that contains the bursty error by identifying a position in the read that is flanked by a match-forwards region that matches a sequence generated by plurality voting from sequences of at least two other reads of the plurality of reads.

13. A system comprising:

means for sequencing a deoxyribose nucleic acid (DNA) strand to generate a plurality of reads, wherein the DNA strand stores digital data;

one or more processing units;

a memory coupled to the one or more processing units, the memory storing instructions that, when executed by the one or more processing units, cause the system to perform acts comprising:

receiving the plurality of reads of the DNA strand that were generated with less than 30× coverage by the means for sequencing that introduces a bursty error that includes multiple adjacent errors into a read of the plurality of reads;

identifying a start of a portion of the read that contains the bursty error by identifying a position in the read that does not match a consensus sequence and is not classified as an insertion, a deletion, or a substitution;

identifying an end of the portion of the read that contains the bursty error by identifying a position in the read that is flanked by a match-backwards region that matches a consensus sequence generated from the plurality of reads;

omitting only the portion of the read that contains the bursty error from generation of a consensus output sequence;

generating the consensus output sequence with portions of the read from either side of the portion of the read that contains the bursty error; and converting the consensus output sequence into digital data.

14. The system of claim 13, wherein the acts further comprise identifying an end of the portion of the read that contains the bursty error by identifying a position in the read that is flanked by a match-forwards region that matches a sequence generated by plurality voting from sequences of at least two other reads of the plurality of reads.

15. The system of claim 13, wherein the means for sequencing is a Nanopore sequencer.

16. The system of claim 13, wherein the plurality of reads are generated with less than 25× coverage.

17. The system of claim 13, wherein the consensus output sequence is generated by comparing values for the plurality of reads at a position of comparison while aligning the plurality of reads with respect to each other based on insertions, deletions, and substitutions.

18. The system of claim 17, wherein comparing values for the plurality of reads comprises determining a plurality consensus base.

\* \* \* \* \*

SEQUENCE LISTING

```
Sequence total quantity: 4
SEQ ID NO: 1          moltype = DNA  length = 14
FEATURE               Location/Qualifiers
misc_feature          1..14
                      note = arbitrary sequence for illustrative purposes
source                1..14
                      mol_type = other DNA
                      organism = synthetic construct
SEQUENCE: 1
agctggacgt aggc                                                  14

SEQ ID NO: 2          moltype = DNA  length = 14
FEATURE               Location/Qualifiers
misc_feature          1..14
                      note = arbitrary sequence for illustrative purposes
source                1..14
                      mol_type = other DNA
                      organism = synthetic construct
SEQUENCE: 2
agattgatct acgc                                                  14

SEQ ID NO: 3          moltype = DNA  length = 14
FEATURE               Location/Qualifiers
misc_feature          1..14
                      note = arbitrary sequence for illustrative purposes
source                1..14
                      mol_type = other DNA
```

-continued

```
                       organism = synthetic construct
SEQUENCE: 3
atcttgagct acgt                                           14

SEQ ID NO: 4           moltype = DNA  length = 14
FEATURE                Location/Qualifiers
misc_feature           1..14
                       note = arbitrary sequence for illustrative purposes
source                 1..14
                       mol_type = other DNA
                       organism = synthetic construct
SEQUENCE: 4
agcctgagcc acgc                                           14
```